United States Patent
He et al.

(10) Patent No.: US 7,223,242 B2
(45) Date of Patent: May 29, 2007

(54) ULTRASOUND IMAGING SYSTEM

(75) Inventors: Xingbai He, Andover, MA (US); Peter P. Chang, Burlington, MA (US); Eric R. Kischell, Pepperell, MA (US); Alice M. Chiang, Weston, MA (US)

(73) Assignee: Teratech Corporation, Burlington, MA (US)

( * ) Notice: Subject to any disclaimer, the term of this patent is extended or adjusted under 35 U.S.C. 154(b) by 0 days.

(21) Appl. No.: 10/259,251

(22) Filed: Sep. 27, 2002

(65) Prior Publication Data

US 2003/0100833 A1 May 29, 2003

Related U.S. Application Data

(63) Continuation-in-part of application No. 09/966,810, filed on Sep. 28, 2001.

(51) Int. Cl.
*A61B 8/06* (2006.01)

(52) U.S. Cl. ........................ 600/454; 600/443
(58) Field of Classification Search ................ 600/437, 600/472, 455, 451, 116, 493, 459, 300, 488, 600/461, 460, 443, 447, 441, 443.4, 47, 454–458; 128/916; 73/861.25; 700/4–5, 73; 701/18–19, 701/48; 708/5; 710/69; 712/2, 7, 20–22
See application file for complete search history.

(56) References Cited

U.S. PATENT DOCUMENTS

| | | | |
|---|---|---|---|
| 4,702,258 A | 10/1987 | Nicolas et al. | 128/660 |
| 4,727,376 A | 2/1988 | Prenat | 342/134 |
| 5,170,791 A | 12/1992 | Boos et al. | 128/661.07 |
| 5,369,624 A | 11/1994 | Fukukita et al. | 367/103 |

(Continued)

FOREIGN PATENT DOCUMENTS

| | | |
|---|---|---|
| EP | 1016875 | 7/2000 |
| JP | 10-73658 | 3/1998 |
| WO | WO 00/31634 | 6/2000 |

OTHER PUBLICATIONS

Kasai, Chihiro; et al., *Real–Time–Dimensional Blood Flow Imaging Using an Autocorrelations Technique*, IEEE Transactions on Sonics and Ultrasonics, vol. SU–32, No. 3, pp. 458–464 May 3, 1985.

*Primary Examiner*—Francis J. Jaworski
(74) *Attorney, Agent, or Firm*—Weingarten, Schurgin, Gagnebin & Lebovici LLP

(57) ABSTRACT

The present invention is directed to an ultrasound imaging system and method for Doppler processing of data. The ultrasonic imaging system efficiently addresses the data computational and processing needs of Doppler processing. Software executable sequences in accordance with a preferred embodiment of the present invention determines the phase shift and the auto-correlation phase of filtered image data. In a preferred embodiment, the system of ultrasonic imaging also includes a sequence of instructions for Doppler processing that provides the functions for demodulation, Gauss Match filtering, auto-correlation calculation, phase shift calculation, frame averaging, and scan conversion implemented with Single Instruction Multiple Data (SIMD) or Multiple Instruction Multiple Data (MIMD) instructions.

In a preferred embodiment, the ultrasound imaging system of the present invention includes a processing module; and memory operable coupled to the processing module, wherein the memory stores operational instructions that cause the processing module to map serial data to vector representation, calculate an auto-correlation function of the data, calculate a phase shift of the auto-correlation function to generate a monotonic function covering all values of the phase shift corresponding to a range of Doppler velocities and display the resultant images, for example, as color images.

20 Claims, 14 Drawing Sheets

U.S. PATENT DOCUMENTS

| | | | |
|---|---|---|---|
| 5,465,095 A | 11/1995 | Bryant | 342/159 |
| 5,653,236 A | 8/1997 | Miller | 128/661.01 |
| 5,690,114 A * | 11/1997 | Chiang et al. | 600/447 |
| 5,722,412 A * | 3/1998 | Pflugrath et al. | 600/459 |
| 5,735,797 A * | 4/1998 | Muzilla et al. | 600/441 |
| 5,830,131 A * | 11/1998 | Caro et al. | 600/300 |
| 5,957,846 A | 9/1999 | Chiang et al. | 600/441 |
| 5,964,709 A * | 10/1999 | Chiang et al. | 600/447 |
| 6,095,980 A * | 8/2000 | Burns et al. | 600/453 |
| 6,111,816 A | 8/2000 | Chiang et al. | 367/7 |
| 6,126,601 A | 10/2000 | Gilling | 600/440 |
| 6,132,379 A * | 10/2000 | Patacsil et al. | 600/459 |
| 6,139,501 A | 10/2000 | Roundhill et al. | 600/440 |
| 6,248,073 B1 | 6/2001 | Gilbert et al. | 600/447 |
| 6,417,797 B1 * | 7/2002 | Cousins et al. | 342/179 |
| 6,417,857 B2 * | 7/2002 | Finger et al. | 345/505 |
| 6,436,040 B1 * | 8/2002 | Collamore et al. | 600/437 |
| 6,530,887 B1 | 3/2003 | Gilbert et al. | 600/459 |
| 6,540,682 B1 * | 4/2003 | Leavitt et al. | 600/447 |
| 2002/0154727 A1 | 10/2002 | Ning | 378/4 |

* cited by examiner

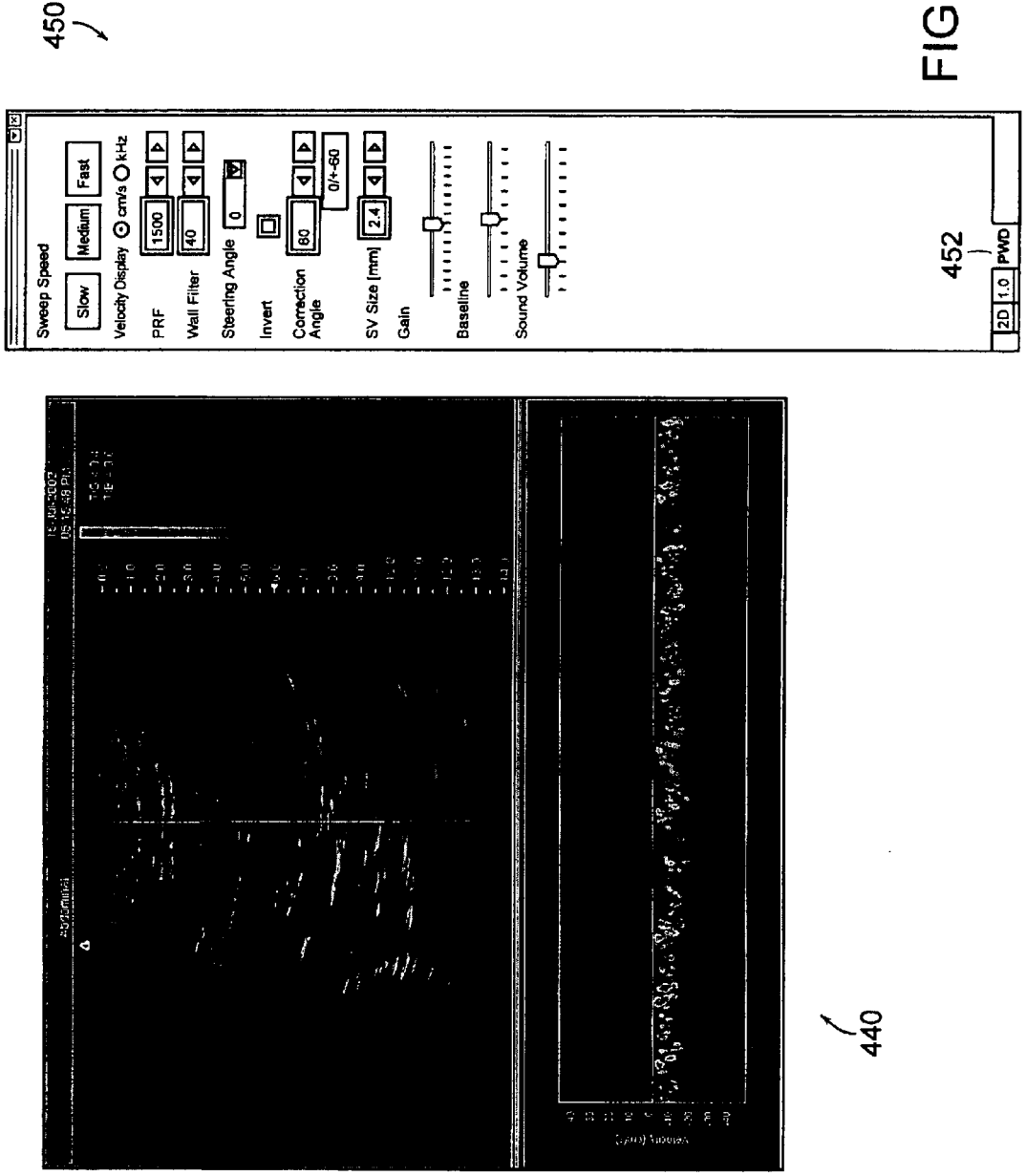
FIG. 13A
FIG. 13B
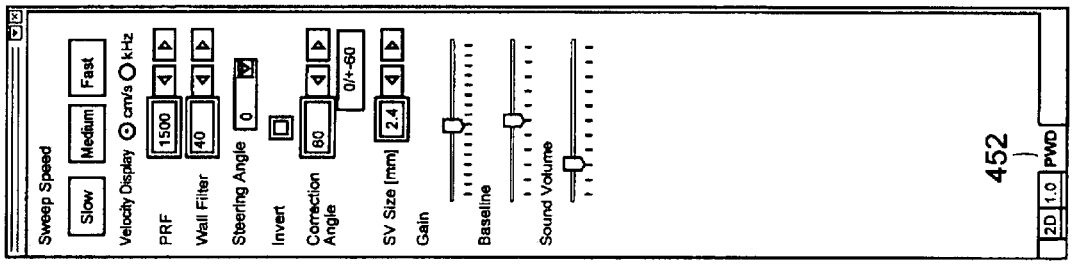
FIG. 13C

ULTRASOUND IMAGING SYSTEM

CROSS REFERENCES TO RELATED APPLICATIONS

The present application is a continuation-in-part of U.S. patent application Ser. No. 09/966,810, filed Sep. 28, 2001.

The entire contents of the above application is incorporated herein by reference in its entirety.

BACKGROUND OF THE INVENTION

Ultrasonic diagnostic equipment has become an indispensable tool for clinical use. For approximately the past twenty years, real-time B-mode ultrasound imagers are used for investigating all soft tissue structures in the human body. One of the recent developments within medical imaging technology is the development of Doppler ultrasound scanners. Doppler ultrasound is an important technique for non-invasively detecting and measuring the velocity of moving structures, and particularly to display an estimate of blood velocity in the body in real time.

The basis of Doppler ultrasonography is the fact that reflected and/or scattered ultrasonic waves from a moving interface undergoes a frequency shift. In general the magnitude and the direction of this shift provides information regarding the motion of this interface. How much the frequency is changed depends upon how fast the object or moving interface is moving. Doppler ultrasound has been used mostly to measure the rate of blood flow through the heart and major arteries.

There are several forms of depiction of blood flow in medical Doppler imaging or more generally different velocity estimation systems that currently exist: Color Flow imaging, power Doppler and Spectral sonogram. Color flow imaging (CFI), interrogates a whole region of the body, and displays a real-time image of mean velocity distribution. CFI provides an estimate of the mean velocity of flow with a vessel by color coding the information and displaying it, super positioned on a dynamic B-mode image or black and white image of anatomic structure. In order to differentiate flow direction, different colors are used to indicate velocity toward and away from the transducer.

While color flow imaging displays the mean or standard deviation of the velocity of reflectors, such as the blood cells in a given region, power Doppler (PD) displays a measurement of the amount of moving reflectors in the area, similarly to the B-mode image's display of the total amount of reflectors. A power Doppler image is an energy image in which the energy of the flow signal is displayed. Thus, power Doppler depicts the amplitude or power of the Doppler signals rather than the frequency shift. This allows detection of a larger range of Doppler shifts and thus better visualization of small vessels. These images give no velocity information, but only show the direction of flow. In contrast, spectral Doppler or spectral sonogram utilizes a pulsed wave system to interrogate a single range gate or sampling volume, and displays the velocity distribution as a function of time. The sonogram can be combined with the B-mode image to yield a duplex image. Typically, the top side displays a B-mode image of the region under investigation, and the bottom displays the sonogram. Similarly, the sonogram can also be combined with the CFI or PD image to yield a triplex image. The time for data acquisition is then divided between acquiring all three sets of data, and the frame rate of the images is typically decreased, compared to either CFI or duplex imaging.

The current ultrasound systems require extensive complex data processing circuitry in order to perform the imaging functions described herein. Doppler processing for providing two-dimensional depth and Doppler information in color flow images, power Doppler images and/or spectral sonograms require millions of operations per second. There exists a need for an ultrasound imaging system that provides for compute-intensive systems and methods to efficiently address the data processing needs of information, such as Doppler processing.

SUMMARY OF THE INVENTION

The present invention is directed to an ultrasound imaging system and method for Doppler processing of data. The ultrasonic imaging system efficiently addresses the data computational and processing needs of Doppler processing. Software executable sequences in accordance with a preferred embodiment of the present invention determines the phase shift and the auto-correlation phase of filtered image data. In a preferred embodiment, the system of ultrasonic imaging also includes a sequence of instructions for Doppler processing that provides the functions for demodulation, Gaussian Match filtering, auto-correlation calculation, phase shift calculation, frame averaging, and scan conversion.

In a preferred embodiment, the processing system includes parallel processing elements which execute Single Instruction Multiple Data (SIMD) or Multiple Instruction Multiple Data (MIMD) instructions. A computer having a Pentium® III processor including MMX™ technology is an exemplary computational device of a preferred embodiment of the ultrasonic imaging system in accordance with the present invention.

A method of the present invention includes imaging a region of interest with ultrasound energy using a portable ultrasound imaging system which in turn includes a transducer array within a handheld probe. An interface unit is connected to the handheld probe with a cable interface. The interface unit has a beamforming device connected to a data processing system with another cable interface. Output signals from the interface unit are provided to the handheld probe to actuate the transducer array, which in turn delivers ultrasound energy to the region of interest. The ultrasound energy returning to the transducer array is collected from the region of interest and transmitted from the handheld probe to the interface unit. A beamforming operation is performed with the beamforming device in the interface unit. The method further includes transmitting data from the interface unit to the data processing system such that the data processing system receives a beamformed electronic representation of the region of interest. The data processing system has at least one parallel processing element integrated with a microprocessor to execute a sequence of instructions for Doppler processing and displaying of Doppler images.

In a preferred embodiment, the ultrasound imaging system of the present invention includes a processing module; and memory operable coupled to the processing module, wherein the memory stores operational instructions that cause the processing module to map serial data to a vector representation, demodulate the data to obtain in-phase and quadrature sample data, calculate an auto-correlation function of the data, calculate a phase shift of the auto-correlation function represented as a monotonic function in the interval corresponding to the range of Doppler velocities according to the Nyquist criterion and expressed as a simple mathematical function, convert the phase shift to an index and display the images, for example, as color images.

Preferred embodiments of the present invention include the portable ultrasound system comprising one of at least a color Doppler mode, a directional power Doppler mode, a power Doppler mode and a pulsed wave Doppler mode. The portable ultrasound system includes adjustable controls for one of at least scan area selection, velocity display, steering angles, color inversion, color gain, color priority, color persistence, color baseline and frame rate.

The foregoing and other features and advantages of the system and method for ultrasound imaging will be apparent from the following more particular description of preferred embodiments of the system and method as illustrated in the accompanying drawings in which like reference characters refer to the same parts throughout the different views.

BRIEF DESCRIPTION OF THE DRAWINGS

FIGS. 13A–13C illustrate a real-time mixed mode (B-mode scan), a pulsed Doppler waveform and the controls provided to a user in a pulsed wave Doppler mode in accordance with a preferred embodiment of the present invention.

Figure 1:
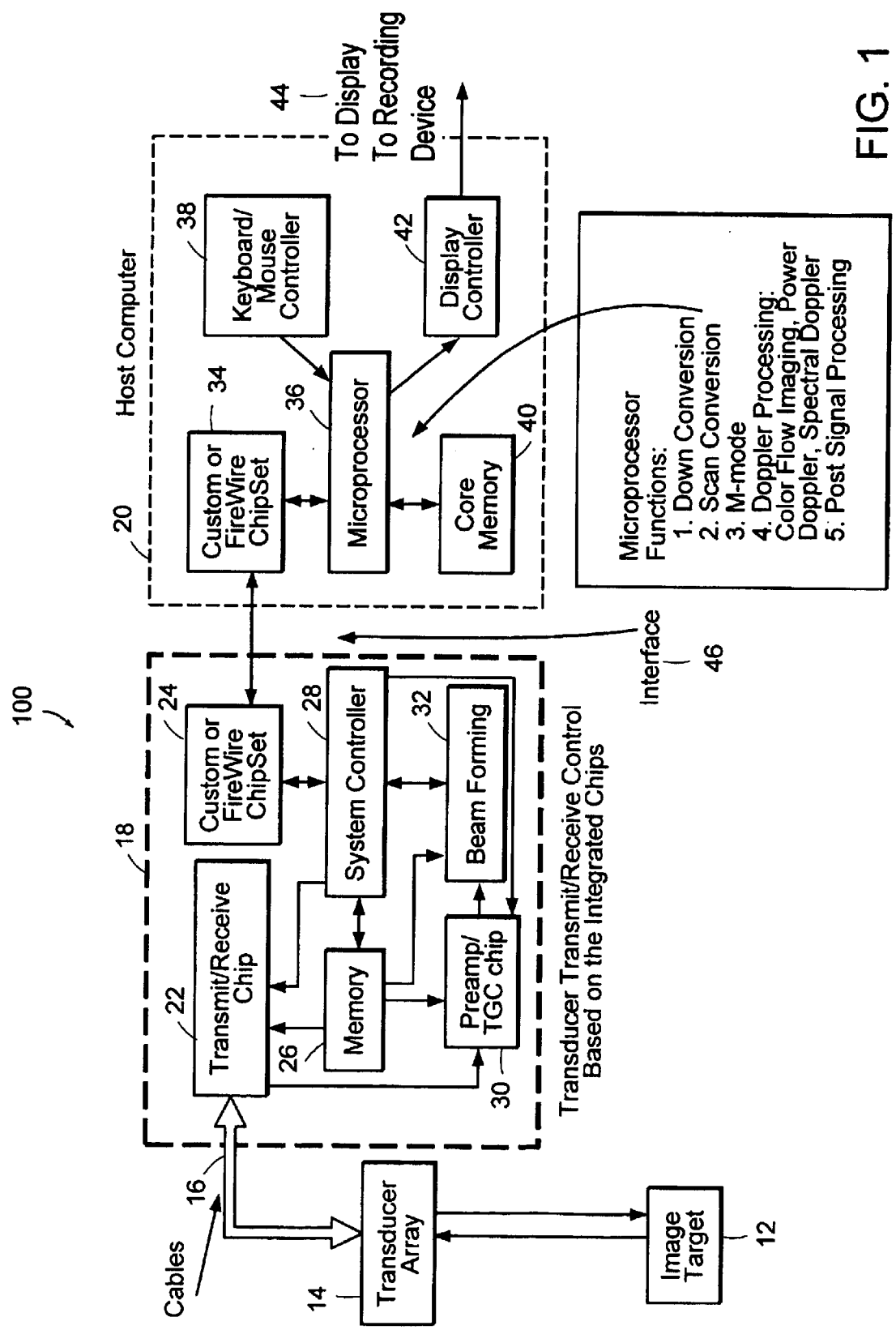
FIG. 1 is a block diagram of a preferred embodiment of the ultrasound imaging system in accordance with the present invention.

The drawings are not necessarily to scale, emphasis instead being placed upon illustrating the principles of the invention.

DETAILED DESCRIPTION OF THE INVENTION

The ultrasound imaging system is directed at a Doppler processing system in a portable ultrasound system. In a preferred embodiment, the ultrasonic imaging system includes parallel computation units and a memory having stored therein instructions to process data and display ultrasound images using computer-efficient methods.

A preferred embodiment of the ultrasound imaging system includes a pulse-Doppler processor for color flow imaging or map applications. Color flow (CF) imaging combines in a single modality the abilities of ultrasound to image tissue and to investigate blood flow. CF images consist of Doppler information that can be color-encoded and superimposed on a B-mode gray-scale image.

Color-flow imaging is a mean velocity estimator. There are two known different techniques for computing the mean velocity. First, in a pulsed Doppler system, Fast-Fourier Transforms (FFTs) can be used to yield the velocity distribution of the region of interest, and both the mean and the variance of the velocity profile can be calculated and displaced as a color flow imaging. The other approach is the one dimensional auto-correlation technique described by Kasai et al in "Real-Time Two Dimensional Blood Flow Imaging Using an Auto-correlation Technique" in the IEEE Transactions on Sonics and Ultrasonics Vol. SU-32, No. 3 in May 1985, the entire contents of which are incorporated herein by reference.

Mean blood flow velocity is estimated from the frequency spectra of echoes. An estimate of the mean velocity in the range gate or sample volume gives an indication of the volume flow rate. As the frequency of the range or depth gated and sampled signal is proportional to the velocity, the spatial mean velocity can be determined by the mean angular frequency of $P(\omega)$ and is expressed as:

$$\bar{\omega} = \frac{\int_{-\infty}^{+\infty} \omega P(\omega) d\omega}{\int_{-\infty}^{+\infty} P(\omega) d\omega} \quad (1)$$

where $P(\omega)$ is the power density spectrum of the received, demodulated signal. Equation (1) gives the mean Doppler frequency shift due to the blood flow. The mean blood flow velocity v can then be estimated by the following equation:

$$\bar{v} = \frac{\bar{\omega}}{\omega_0} \frac{c}{2\cos\theta} \quad (2)$$

where c is the velocity of sound and θ the angle between the sound beam and the blood flow vector.

The extent of turbulence in blood flow may be inferred from the variance of the spectrum. Since the Doppler frequency directly relates to the flow vector, i.e., flow direction and speed, in an ultrasonic sample volume, the spectrum spread broadens in accordance with flow disturbance. While in laminar flow, the spectrum spread is narrow, since a uniform flow vector gives a singular Doppler frequency shift. The mean angular frequency can be determined by the phase-shift of auto-correlation of the complex signal z(t). The inverse Fourier transform of the power density spectrum is the auto-correlation function $R(\tau)$ and is expressed as:

$$R(\tau) = \int_{-\infty}^{+\infty} P(\omega) e^{j\omega\tau} d\omega \equiv A(\tau) e^{j\phi(\tau)} \quad (3)$$

From the moment's theorem of Fourier transforms, it can be shown that $$\dot{R}(0) = j \int_{-\infty}^{+\infty} \omega P(\omega) d\omega \quad \text{and} \quad (4)$$

$$R(0) = \int_{-\infty}^{+\infty} P(\omega) d\omega \quad (5)$$

It follows then $$\overline{\omega} = \frac{\dot{R}(0)}{jR(0)} \quad (6)$$

Therefore, the mean velocity estimation can be reduced to an estimation of the auto-correlation and the derivative of the auto-correlation. The estimator given by the above expression can be calculated when data from two returned lines are used. From Equation (3), $$\dot{R}(0) = jA(0)\dot{\phi}(0) \text{ and } R(0) = A(0) \quad (7)$$

Substituting the above equations into (6), we have $$\overline{\omega} = \dot{\phi}(0) \approx \frac{\phi(1) - \phi(-1)}{2} = \phi(1) \quad (8)$$

Generally, $\phi(1)$ can be determined by either of the following methods $$\phi(1) = \arctan\left(\frac{Im\{R(1)\}}{Re\{R(1)\}}\right) \quad (9)$$

$$\phi(1) = \arcsin\left(\frac{m\{R(1)\}}{|R(1)|}\right) \quad (10)$$

$$\phi(1) = \arccos\left(\frac{Re\{R(1)\}}{|R(1)|}\right) \quad (11)$$

In a preferred embodiment of the ultrasonic imaging system, $$sign(\phi(1))\sin^2\left(\frac{\phi(1)}{2}\right)$$

represents the phase-shift, where $$sign(x) = \begin{cases} 1 & x > 0 \\ 0 & x = 0 \\ -1 & x < 0 \end{cases} \quad (12)$$

$$sign(\phi(1))\sin^2\left(\frac{\phi(1)}{2}\right)$$

is a monotonic function of $\phi(1)$ in the interval $(-\pi, +\pi)$. Thus, every value of $$sign(\phi(1))\sin^2\left(\frac{\phi(1)}{2}\right)$$

uniquely defines a $\phi(1)$ in the interval $(-\pi, +\pi)$ and vice versa.
Further, $$sign(\phi(1)) = sign(\sin(\phi(1))) = sign(Im\{R(1)\}) \quad (13)$$

$$\sin^2\left(\frac{\phi(1)}{2}\right) = \frac{1 - \cos(\phi(1))}{2} = \frac{1 - \frac{Re\{R(1)\}}{|R(1)|}}{2} \quad (14)$$

And therefore:

$$sign(\phi(1))\sin^2\left(\frac{\phi(1)}{2}\right) = \frac{1}{2}sign(Im\{R(1)\})\left[1 - \frac{Re\{R(1)\}}{|R(1)|}\right] \quad (15)$$

Similarly, the $\phi(1)$ can be determined based on $$\tan\left(\frac{\phi(1)}{2}\right) = \frac{\sin\phi(1)}{1 + \cos(\phi(1))} = \frac{\frac{Im\{R(1)\}}{|R(1)|}}{1 + \frac{Re\{R(1)\}}{|R(1)|}} \quad (15a)$$

In a preferred embodiment of the present invention, the estimator given by the above expressions 15 and/or 15(a) can be calculated when data from at least two returned lines are used. The equations 15 and 15a represent the phase shift $\phi$ as a monotonic function in the interval between negative and positive pi $(-\pi,+\pi)$ and express the phase shift as simple mathematical calculations. In a preferred embodiment of the present invention, more lines are used in order to improve the signal-to-noise ratio. Data from several RF lines are needed in order to get useful velocity estimates by the auto-correlation estimator. Preferably, in a particular embodiment between eight (8) and sixteen (16) lines are acquired for the same image direction. The lines are divided into range gates throughout the image depths, and the velocity is estimated along the lines.

The CFI pulses are interspersed between the B-mode image pulses in duplex imaging. It is known that a longer duration pulse train gives an estimator with a lower variation. However, a good spatial resolution necessitates a short pulse. In a particular embodiment of the ultrasound imaging system of the present invention, a separate pulse is preferably used for the B-mode image, because the CFI pulse is too long for high quality gray-scale image.

While Color Flow Imaging (CFI) sonograph has been an effective diagnostic tool in clinical cardio-vascular application, power Doppler (PD) imaging provides an alternative method of displaying the blood stream in the insonified regions of interest. While CF imaging displays the mean or standard deviation of the velocity of reflectors such as, for example, blood cells in a given region, PD displays a measurement of the amount of moving reflectors in the area, similarly to the B-mode image's display of the total amount of reflectors. Thus, power Doppler is akin to a B-mode image with the stationary reflectors suppressed. This is particularly useful for viewing small moving particles with small scattering cross-sections such as red blood cells.

The power Doppler image displays the integrated Doppler power instead of the mean frequency shift as used for color Doppler imaging. As discussed hereinbefore, the color flow mapping is a mean frequency estimation, and can be expressed as:

$$\overline{\omega} = \frac{\int_{-\infty}^{+\infty} \omega P(\omega) d\omega}{\int_{-\infty}^{+\infty} P(\omega) d\omega} \quad (1)$$

where $\overline{\omega}$ represents the mean frequency shift and $P(\omega)$ is the power density spectrum of the received signal. It has also been shown hereinbefore by inverse Fourier transform that $$R(\tau) = \int_{-\infty}^{+\infty} P(\omega)e^{j\omega\tau} d\omega \qquad (16)$$

The total integrated Doppler power can be expressed as $$pw = \int_{-\infty}^{+\infty} P(\omega) d\omega \qquad (17)$$

Substituting Equation (16) into (17), it follows that $$R(0) = \int_{-\infty}^{+\infty} P(\omega)\exp(j\omega 0) d\omega = \int P(\omega) d\omega = pw \qquad (18)$$

and that the 0th lag of the auto-correlation function can be used to compute the integrated total Doppler power. In other words the integrated power in the frequency domain is the same as the integrated power in the time domain and hence the power Doppler can be computed in one preferred embodiment from either time-domain or the frequency-domain data. In either embodiment, the unwanted signal from the surrounding tissue such as the vessel walls is removed via filtering.

In a preferred embodiment, the PD computation can be carried out in software executing a sequence of instructions on the host processor similarly to the computation of the CFI processing described hereinbefore. In a preferred embodiment, parallel computation units such as those in the Intel® Pentium® and Pentium® III's MMX™ coprocessors that allow rapid computation of the required functions are used. Intel®'s MMX™ is a Pentium® microprocessor that executes applications faster than non-MMX™ Pentium® microprocessor. It is designed to improve the performance of multimedia and communication algorithms. The technology includes new instructions and data types which achieve higher levels of performance for these algorithms or host processors. In particular, MMX™ Pentium® microprocessors have microprocessor instructions that are designed to handle video, audio and graphical data more efficiently. Further, MMX™ technology consists of a Single Instruction Multiple Data (SIMD) process which makes it possible for one instruction to perform the same operation on multiple data items. In addition, the memory cache on the MMX™ Processor has increased to, for example, 32 thousand bytes, which provides for fewer accesses to memory that is off the microprocessor. In an alternate preferred embodiment, a Digital Signal Processor (DSP) can also be used to perform the processing function. Such architecture permits flexibility in changing digital signal processing algorithms and transmitting signals to achieve the best performance as the region of interest is changed.

As discussed hereinbefore, the frequency content of the Doppler signal corresponds to the velocity distribution of the blood. It is common to device a system for estimating blood movement at a fixed depth in tissue. A transmitter emits an ultrasound pulse that propagates into and interacts with tissue and blood. The backscattered signal is received by the same transducer and amplified. For a multiple-pulsed system, one sample is acquired for each pulse emitted. A display of the distribution of velocities can be made by Fourier transforming the received signal and displaying the result. This display is also called a sonogram. Often a B-mode image is presented along with the sonogram in a duplex system, and the area of investigation or range gate is displayed on the image. The placement and size of the range gate are determined by the user, and this determines the time instance for the sampling operation. The range gate length determines the area of investigation and sets the length of the emitted pulse.

The calculated spectral density is displayed on a screen with frequency on the y-axis and time on the x-axis. The intensity at a point on the screen indicates the amplitude of the spectrum and is, thus, proportional to the number of blood scatterer moving at a particular velocity.

FIG. 1 is a schematic functional block of one embodiment of the ultrasound imaging system 10 of the invention. Similar imaging systems are described in U.S. Pat. No. 5,957,846 to Alice M. Chiang et al., issued Sep. 28, 1999, entitled "Portable Ultrasound Imaging System," the entire contents of which are being incorporated herein by reference. As shown, the system 10 includes an ultrasonic transducer array 14 which transmits ultrasonic signals into a region of interest or image target 12, such as a region of human tissue, and receives reflected ultrasonic signals returning from the image target. The system 10 also includes a front-end interface or processing unit 18 which is connected by cables 16, for example, coaxial cables to the transducer array 14 and includes a transducer transmit/receive control chip 22.

Ultrasonic echoes reflected by the image target 12 are detected by the ultrasonic transducers in the array 14. Each transducer converts the received ultrasonic signal into a representative electrical signal which is forwarded to an integrated chip having preamplification circuits and time-varying gain control (TGC) circuitry 30. The preamplification circuitry sets the level of the electrical signals from the transducer array 14 at a level suitable for subsequent processing, and the TGC circuitry is used to compensate for attenuation of the sound pulse as it penetrates through human tissue and also drives the beamforming circuits 32 to produce a line image. The conditioned electrical signals are forwarded to the beamforming circuitry 32 which introduces appropriate differential delay into each of the received signals to dynamically focus the signals such that an accurate image can be created. Further details of the beamforming circuitry 32 and the delay circuits used to introduce differential delay into received signals and the pulses generated by a pulse synchronizer are described in U.S. Pat. No. 6,111,816 to Alice M. Chiang et al., issued Aug. 29, 2000 entitled "Multi-Dimensional Beamforming Device," the entire content of which are being incorporated herein by reference.

A memory 30 stores data from a controller 28. The memory 30 provides stored data to the transmit/receive chip 22, the TGC 30 and the beamformer 32. The output from the system controller 28 is connected directly to a custom or FireWire Chipset. The FireWire Chipset is described in co-pending U.S. patent application Ser. No. 09/449,780, entitled "Ultrasound Probe with Integrated Electronics," by Jeffrey M. Gilbert et al., the entire contents of which are being incorporated herein by reference. "FireWire" refers to IEEE standard 1394, which provides high-speed data transmission over a serial link. There also exists a wireless version of the FireWire standard allowing communication via an optical link for untethered operation.

The FireWire standard and an ultrasound probe with integrated electronics as described in co-pending U.S. patent application Ser. No. 09/791,491, entitled "Ultrasound Probe With Integrated Electronics," by Alice M. Chiang et al., the entire contents of which are being incorporated herein by reference, may be used in preferred embodiments of the present invention. The FireWire standard is used for multimedia equipment and allows 100–200 Mbps and preferably in the range of 400–800 Mbps operation over an inexpensive 6 wire cable. Power is also provided on two of the six wires so that the FireWire cable is the only necessary electrical connection to the probe head. A power source such as a battery or IEEE1394 hub can be used. The FireWire protocol provides both isochronous communication for transferring high-rate, low-latency video data as well as asynchronous, reliable communication that can be used for configuration and control of the peripherals as well as obtaining status information from them. Several chipsets are available to interface custom systems to the FireWire bus. Additionally, PCI-to-FireWire chipsets and boards are currently available to complete the other end of the head-to-host connection. CardBus-to-FireWire boards can also be used.

Although the VRAM controller directly controls the ultrasound scan head, higher level control, initialization, and data processing and display comes from a general purpose host such as a desktop PC, laptop, or palmtop computer. The display can include a touchscreen capability. The host writes the VRAM data via the VRAM Controller. This is performed both at initialization as well as whenever any parameters change (such as number or positions of zones, or types of scan head) requiring a different scanning pattern. During routine operation when data is just being continually read from the scan head with the same scanning parameters, the host need not write to the VRAM. Because the VRAM controller also tracks where in the scan pattern it is, it can perform the packetization to mark frame boundaries in the data that goes back to the host. The control of additional functions such as power-down modes and querying of buttons or dial on the head can also be performed via the FireWire connection.

Although FireWire chipsets manage electrical and low-level protocol interface to the FireWire interface, the system controller has to manage the interface to the FireWire chipset as well as handling higher level FireWire protocol issues such as decoding asynchronous packets and keeping frames from spanning isochronous packet boundaries.

Asynchronous data transfer occurs at anytime and is asynchronous with respect to the image data. Asynchronous data transfers take the form of a write or read request from one node to another. The writes and the reads are to a specific range of locations in the target node's address space. The address space can be 48 bits. The individual asynchronous packet lengths are limited to 1024 bytes for 200 Mbps operation. Both reads and writes are supported by the system controller. Asynchronous writes are used to allow the host to modify the VRAM data as well as a control word in the controller which can alter the operation mode. Asynchronous reads are used to query a configuration ROM (in the system controller FPGA) and can also be used to query external registers or I/O such as a "pause" button. The configuration ROMs contain a querible "unique ID" which can be used to differentiate the probe heads as well as allow node-lockings of certain software features based on a key.

Using isochronous transfers, a node reserves a specified amount of bandwidth and it gets guaranteed low-overhead bursts of link access every $1/8000$ second. All image data from the head to the host is sent via isochronous packets. The FireWire protocol allows for some packet-level synchronization and additional synchronization is built into the system controller.

The front-end processing or interface unit system controller 28 interfaces with a host computer 20, such as a desktop PC, laptop or palmtop, via the custom or FireWire Chipsets 24, 34. This interface allows the host to write control data into the memory 26 and receive data back. This may be performed at initialization and whenever a change in parameters such as, for example, number and/or position of zones, is required when the user selects a different scanning pattern. The front-end system controller 28 also provides buffering and flow control functions, as data from the beamformer is sent to the host via a bandwidth-constrained link, to prevent data loss.

The host computer 20 includes a keyboard/mouse controller 38, and a display controller 42 which interfaces with a display or recording device 44. A graphical user interface described in co-pending U.S. patent application Ser. No. 09/822,764 entitled "Unitary Operator Control for Ultrasonic Imaging Graphical User Interface," by Michael Brodsky, the entire contents of which are being incorporated herein by reference, may be used in a preferred embodiment of the present invention.

The host computer further includes a processing unit such as microprocessor 36. In a preferred embodiment of the ultrasound imaging system in accordance with the present invention the microprocessor 36 includes on-chip parallel processing elements. In a preferred embodiment, the parallel processing elements may include a multiplier and an adder. In another preferred embodiment, the processing elements may include computing components, memories, logic and control circuits. Depending on the complexity of the design, the parallel processing elements can execute either SIMD or Multiple Instruction Multiple Data (MIMD) instructions.

Further, the host computer includes a memory unit 40 that is connected to the microprocessor 36 and has a sequence of instructions stored therein to cause the microprocessor 36 to provide the functions of down conversion, scan conversion, M-mode, and Doppler processing which includes color flow imaging, power Doppler and spectral Doppler, and any post-signal processing. The down conversion or mixing of sampled analog data may be accomplished by first multiplying the sampled data by a complex value and then filtering the data to reject images that have been mixed to nearby frequencies. The outputs of this down-conversion processing are available for subsequent display or Doppler processing.

The scan conversion function converts the digitized signal data from the beamforming circuitry 32 from polar coordinates $(r,\theta)$ to rectangular coordinates $(x,y)$. After the conversion, the rectangular coordinate data can be forwarded for optional post signal processing where it is formatted for display on the display 44 or for compression in a video compression circuit. Scan conversion and beamforming and associated interfaces are described in U.S. Pat. No. 6,248,073 to Jeffrey M. Gilbert et al., issued on Jun. 19, 2001, entitled "Ultrasound Scan Conversion with Spatial Dithering," the entire contents of which are being incorporated herein by reference.

The Doppler processing (CFI, PD, spectral Doppler) is used to image target tissue 12 such as flowing blood. In a preferred embodiment, with pulsed Doppler processing, a color flow map is generated. In a preferred embodiment, the CFI, PD, Spectral Doppler computation can be carried out in software running on the host processor. Parallel computation units such as those in the Intel® Pentium® and Pentium® III's MMX™ coprocessors allow rapid computation of the required functions. For parallel processing computation, a plurality of microprocessors are linked together and are able to work on different parts of a computation simultaneously. In another preferred embodiment, digital Signal Processor (DSP) can also be used to perform the task. Such arrangement permits flexibility in changing digital signal processing algorithms and transmitting signals to achieve the best performance as region of interest is changed.

Single Instruction Multiple Data (SIMD) parallel processors allow one micro-instruction to operate at the same time on multiple data items to accelerate software processing and thus performance. One chip provides central coordination in the SIMD parallel processing computer. Currently, SIMD allows the packing of four single precision 32-bit floating point values into a 128-bit register. These new data registers enable the processing of data elements in parallel. Because each register can hold more than one data element, the processor can process more than one data element simultaneously. In a preferred embodiment of the present invention, all the data is organized efficiently to use SIMD operations. In a particular embodiment, Multiple Instruction Multiple Data (MIMD) parallel processors may be used, which include a plurality of processors. Each processor can run different parts of the same executable instruction set and execute these instructions on different data. This particular embodiment employing MIMD may be more flexible than the embodiment utilizing SIMD, however may be more expensive. All the kernel functions such as demodulation, Gauss match filtering, Butterworth high pass filtering, auto-correlation calculation, phase-shift calculation, frame averaging, color-averaging, spatial domain low-pass filtering, and scan conversion interpolation are implemented with SIMD or MIMD. The Doppler processing results in the processed data being scan converted wherein the polar coordinates of the data are translated to rectangular coordinates suitable for display or video compression.

The control circuit, preferably in the form of a microprocessor 36 inside of a personal computer (e.g., desktop, laptop, palmtop), controls the high-level operation of the ultrasound imaging system 10. The microprocessor 36 or a DSP initializes delay and scan conversion memory. The control circuit 36 controls the differential delays introduced in the beamforming circuitry 32 via the memory 26.

The microprocessor 36 also controls the memory 40 which stores data. It is understood that the memory 40 can be a single memory or can be multiple memory circuits. The microprocessor 36 also interfaces with the post signal processing functional instructions and the display controller 44 to control their individual functions. The display controller 44 may compress data to permit transmission of the image data to remote stations for display and analysis via a transmission channel. The transmission channel can be a modem or wireless cellular communication channel or other known communication method.

Figure 2A:
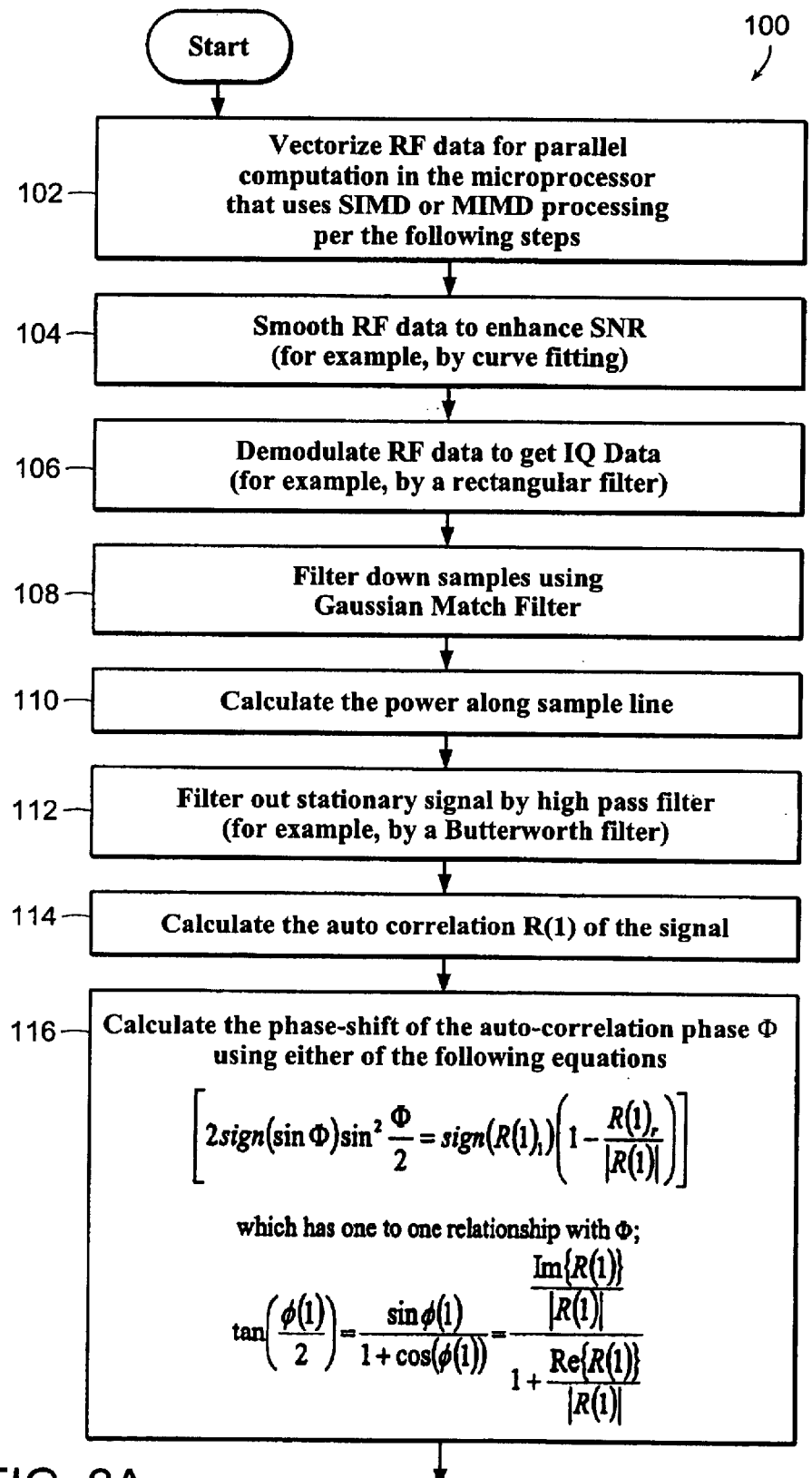
FIGS. 2A and 2B are flow charts of a preferred embodiment of a method for Doppler processing in accordance with the present invention.
Figure 2B:
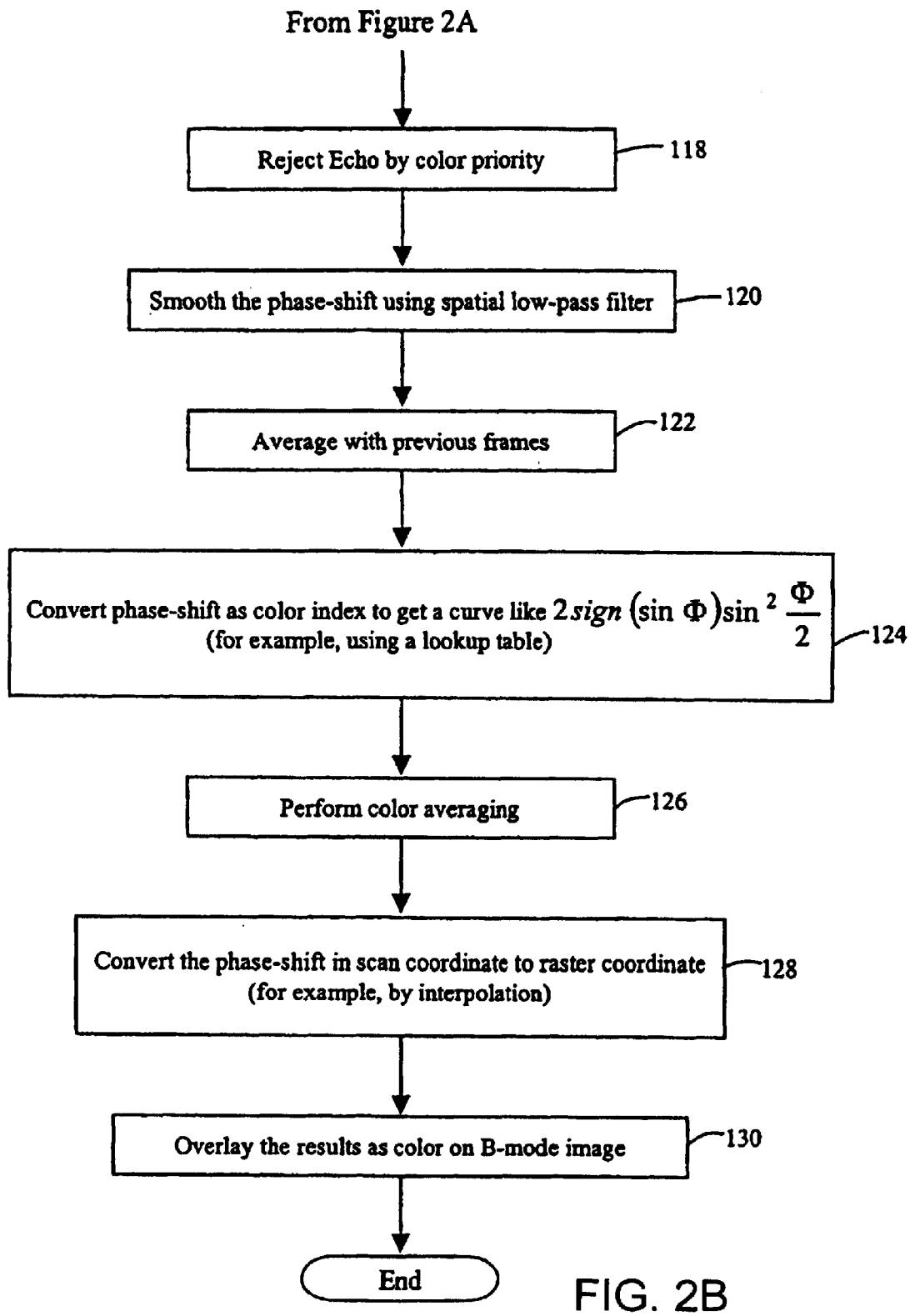

The preferred embodiments of the ultrasonic imaging system address the main problem of performing Doppler processing by software which typically is the speed for processing in real time. FIG. 2 illustrates a preferred embodiment of a method 100 for Doppler processing in accordance with the present invention.

Figure 3:
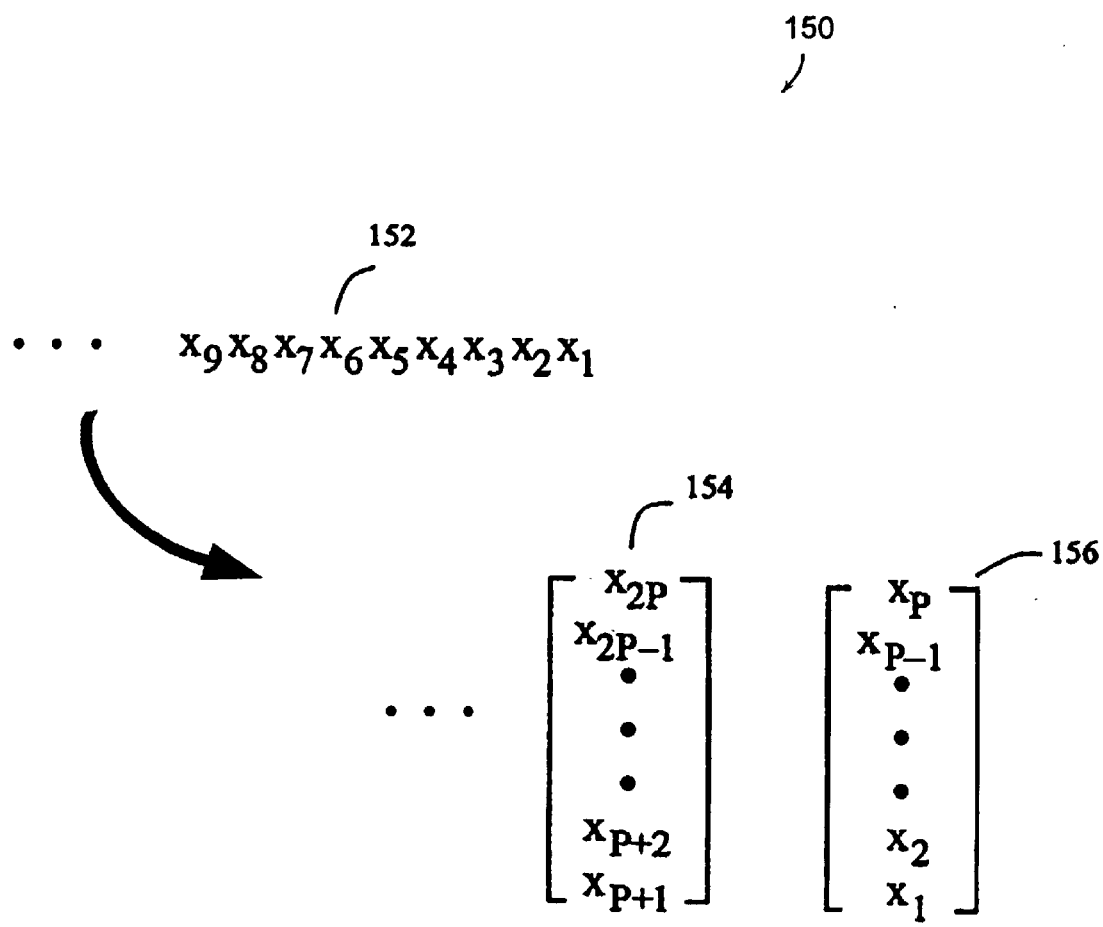
FIG. 3 is a diagram illustrating a preferred embodiment of a method of data mapping for parallel computation in accordance with the present invention.

The method 100 includes mapping or vectorizing of the serial input RF data for parallel computation per step 102. Further details of the data mapping process are described in FIG. 3 which diagrammatically illustrates a preferred embodiment of a method 150 for data mapping for parallel processing. An input data steam 152 is mapped into an input vector representation. The vectors 154, 156 are sequentially provided to the microprocessor's 36 parallel processing elements in which an instruction can be executed that allows all data within the vectors 154, 156 to be operated on in parallel. The dimension of the vector P is determined by the hardware constraints of the microprocessor and may equal the number of parallel processors. For example, current MMX™ technology allows a vector with four dimensions, thus limiting the processing of four dimension vectors in parallel. The dimensions of the vector representation are not limited to the current available technology and can accommodate increases in the dimension of the vector representation.

The method 100 includes the step 104 of smoothing the RF data to enhance the signal to noise ratio (SNR), for example, by curve fitting techniques. The RF data is then demodulated to generated IQ data, where I represents in-phase and Q represents quadrature samples in step 106. Demodulation may be performed, but is not limited to, by a rectangular filter.

In a preferred embodiment, Doppler processing is operated on each sub-segment instead of each single sample. This method saves processing time because the number of sub-segments is much less than number of samples. This is important for clinical use of software-based Doppler products, where a real-time system is critical. Further, by processing sub-segments the sensitivity to flows increases. The data processed per a sequence of instructions in a preferred embodiment represents the average over a segment, which has higher signal to noise ratio.

The use of data segments may however cause lower spatial resolution. To reduce such an effect, the signal sequence is not divided as individual segments, instead each adjoining segment is overlapped with each other. In other words, the center distance or down-sample space between each segment is less than the length of segments. According to the Nyquist sampling theorem, if such a distance is less or equal to the half segment length, the spatial resolution can be recovered by proper interpolation methods. For example, if there exists a demodulated IQ data sequence $y_0, y_1, y_2, y_3, y_4, y_5, y_6, y_7$, the segment length as four and down-sample space as two, a down-sampled data sequence $z_0, z_1, Z_2$, is generated where $z_0$ is the average of $y_0, y_1, y_2, y_3, z_1$ is average of $y_2, y_3, y_4, y_5, z_2$ is the average of $y_4, y_5, y_6, y_7$. Mathematically, the average over each segment can be expressed as $$z(t) = \frac{1}{L} \operatorname{Re} ct\left(\frac{t}{L}\right) * y(t) \tag{19}$$

where y(t) is demodulated complex IQ data, $$\operatorname{Re} ct(t) = \begin{cases} 1 & -0.5 \le t \le 0.5 \\ 0 & \text{Otherwise} \end{cases} \tag{20}$$

If the down-sample space is $\Delta t \le L/2$, then the down-sampled data can be expressed as $$z_s(k) = z(k\Delta t) \text{ where } k=0,1,2, \tag{21}$$

The method 100 further includes the step 108 of filtering the down-samples using, for example, without limitation, the Gauss Match filter. A match filter is used to maximize the signal-to-noise ratio. The signal for Doppler processing is generated by performing quadrature demodulation with the emitted frequency ($\omega_0$) and then Gauss Match filtering the complex signal.

$$y(t) = \operatorname{Gauss}(t) * [rf(t) \exp(j\bar{\omega}_0 t)] \tag{22}$$

where rf(t) is the raw RF data. To save the calculation time, match filtering is only performed on down-sampled samples. From (19), it follows $$z(t) = \text{Re } ct(t) * \text{Gauss}(t) * [rf(t)\exp(j\overline{\omega}_0 t)] \quad (23)$$

Equation (23) can be also expressed as $$z(t) = \text{Gauss}(t) * x(t) \quad (24)$$

$$x(t) = \text{Re } ct(t) * [rf(t)\exp(j\overline{\omega}_0 t)] \quad (25)$$

Thus, the down-sampled data can be expressed as $$z_s(k) = z(k\Delta t) = \int_{-\infty}^{+\infty} \text{Gauss}(\tau) x(k\Delta t - \tau) d\tau \quad (26)$$

The method 100 further includes the step 110 of calculating the power along the sample line before a high pass filter or wall filter. Per step 112, stationary signals are filtered out by a high pass filter, for example, but not limited to, a Butterworth filter. The method 100 then proceeds to step 114 wherein the auto-correlation function R(1) of the signal is calculated.

Per step 116, the phase shift of the auto-correlation phase is then calculated efficiently. As described hereinbefore, the mean velocity can be determined by the mean angular frequency $$\overline{\omega} = \frac{\int_{-\infty}^{+\infty} \omega P(\omega) d\omega}{\int_{-\infty}^{+\infty} P(\omega) d\omega} \quad (27)$$

where $P(\overline{\omega})$ is the power density spectrum of Doppler signal. The mean blood flow velocity $\overline{v}$ can then be estimated by the following equation $$\overline{v} = \frac{\overline{\omega}}{\omega_0} \frac{c}{2\cos\theta}$$

where c is the velocity of sound and θ the angle between the sound beam and the blood flow vector. It has been shown that:

$$\overline{\omega} = \dot{\phi}(0) \approx \frac{\phi(1) - \phi(-1)}{2} = \phi \quad (28)$$

Generally, φ(1) can be determined by either of the following methods $$\phi(1) = \arctan\left(\frac{\text{Im}\{R(1)\}}{\text{Re}\{R(1)\}}\right) \quad (29)$$

$$\phi(1) = \arcsin\left(\frac{\text{Im}\{R(1)\}}{|R(1)|}\right) \quad (30)$$

$$\phi(1) = \arccos\left(\frac{\text{Re}\{R(1)\}}{|R(1)|}\right) \quad (31)$$

All these operations are too time consuming to be implemented by software. Besides, these functions are not monotonic in the interval between −pi and +pi (−π, +π). Thus, not all values of the phase shift corresponding to the range of Doppler velocities according to the Nyquist criterion are accounted for. In a preferred embodiment of the Doppler processing system in accordance with the present invention $$\text{sign}(\phi(1))\sin^2\left(\frac{\phi(1)}{2}\right)$$

represents the phase-shift, where $$\text{sign}(x) = \begin{cases} 1 & x > 0 \\ 0 & x = 0 \\ -1 & x < 0 \end{cases} \quad (32)$$

$$\text{Sign}(\phi(1))\sin^2\left(\frac{\phi(1)}{2}\right)$$

is a monotonic function of φ(1) in the interval (−π,+π). In other words, every value of $$\text{sign}(\phi(1))\sin^2\left(\frac{\phi(1)}{2}\right)$$

uniquely defines a φ(1) in the interval (−π, +π) and vice versa. Calculation of the $\sin^2$ function avoids the use of a square root operation, which is computationally intensive. As we know $$\sin^2\left(\frac{\phi(1)}{2}\right) = \frac{1 - \cos(\phi(1))}{2} = \frac{1 - \frac{\text{Re}\{R(1)\}}{|R(1)|}}{2} \quad \text{So} \quad (34)$$

$$\text{sign}(\phi(1))\sin^2\left(\frac{\phi(1)}{2}\right) = \frac{1}{2}\text{sign}(\text{Im}\{R(1)\})\left[1 - \frac{\text{Re}\{R(1)\}}{|R(1)|}\right] \quad (35)$$

Similarly, the angle phi φ(1) may be also calculated by $$\tan\left(\frac{\phi(1)}{2}\right) = \frac{\sin\phi(1)}{1 + \cos(\phi(1))} = \frac{\frac{\text{Im}\{R(1)\}}{|R(1)|}}{1 + \frac{\text{Re}\{R(1)\}}{|R(1)|}} \quad (35a)$$

The method 100 further includes the step 118 wherein the echo signals are rejected by color priority. In a preferred embodiment, if the power before the high pass filter is larger than a predetermined threshold, the phase shift is set to zero. Per step 120 the phase shift is smoothed by, but is not limited to, a spatial low-pass filter. The phase-shift is averaged with previous frames such as, for example, the previous two frames per step 122. The phase shift is converted to a color index per step 124 to obtain a curve like the one represented by the phase shift calculation in equations 35 and 35a. In a preferred embodiment, a look up table may be used, but is not limited to, in order to convert the phase shift to a color index. Color averaging is then performed per step 126. Per step 128 the phase shift represented in scan coordinates is transformed or converted to raster coordinates using, for example, but is not limited to, interpolation methods. The resultant color images are superpositioned on the B-mode image in step 130.

Figure 4A:
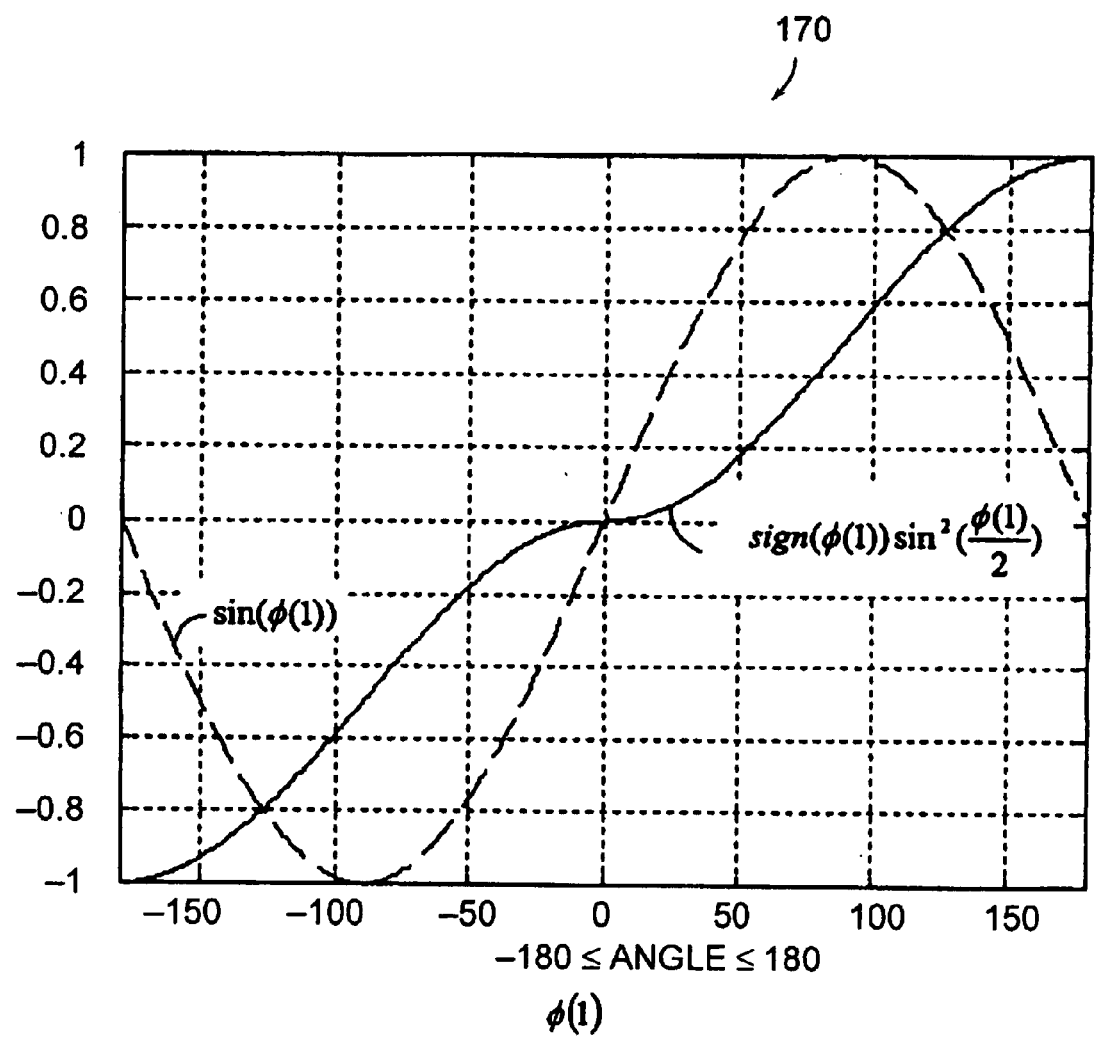
FIGS. 4A and 4B are graphical representations of the Doppler phase shift calculations in accordance with preferred embodiments of the present invention.

FIG. 4A illustrates a graphical representation 170 of the Doppler phase shift calculations, in particular for the following equations 10 and 15 described hereinbefore. The graphical representation of equation 15 in accordance with a preferred embodiment, is a monotonic function in the interval between −pi and pi which spans the range of Doppler velocities according due to the Nyquist criterion. This can be expressed by simple mathematical operations, as shown in the right hand side of equation 15.

$$\phi(1) = \arcsin\left(\frac{\text{Im}\{R(1)\}}{|R(1)|}\right) \quad (10)$$

$$sign(\phi(1))\sin^2\left(\frac{\phi(1)}{2}\right) = \frac{1}{2}sign(\text{Im}\{R(1)\})\left[1 - \frac{\text{Re}\{R(1)\}}{|R(1)|}\right] \quad (15)$$

Figure 4B:
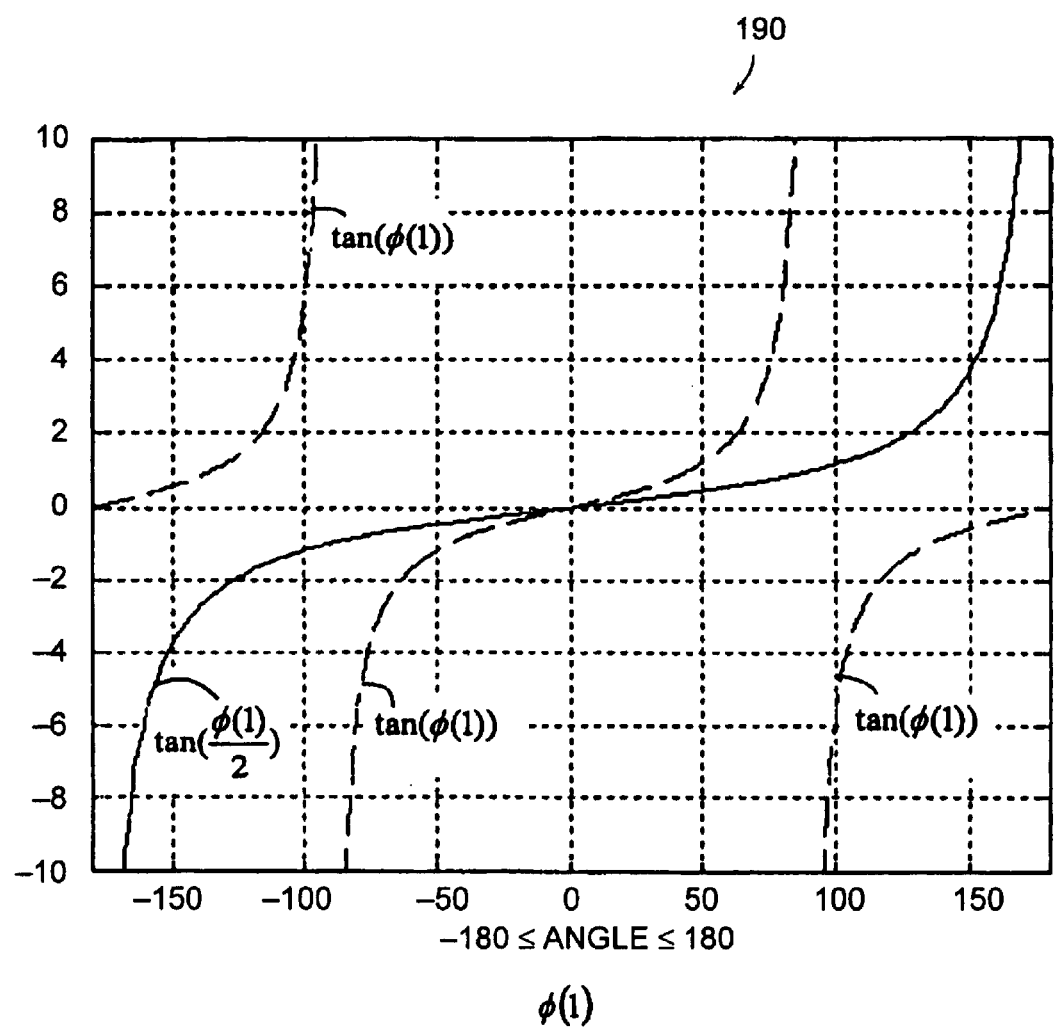

FIG. 4B illustrates a graphical representation 190 of equations 9 and 15a.

$$\phi(1) = \arctan\left(\frac{\text{Im}\{R(I)\}}{\text{Re}\{R(1)\}}\right) \quad (9)$$

$$\tan\left(\frac{\phi(1)}{2}\right) = \frac{\sin\phi(1)}{1 + \cos(\phi(1))} = \frac{\frac{\text{Im}\{R(1)\}}{|R(1)|}}{1 + \frac{\text{Re}\{R(1)\}}{|R(1)|}} \quad (15a)$$

Equation 15a, is the graphical representation of a preferred embodiment, and is a monotonic function in the interval between −pi and pi which spans the range of Doppler velocities according to the Nyquist criterion, and can be expressed by simple mathematical operations, as shown in the right hand side of equation 15a.

It should be noted that an operating environment for the system 10 includes a processing system with at least one high speed processing unit and a memory system. In accordance with the practices of persons skilled in the art of computer programming, the present invention is described with reference to acts and symbolic representations of operations or instructions that are performed by the processing system, unless indicated otherwise. Such acts and operations or instructions are sometimes referred to as being "computer-executed", or "processing unit executed."

It will be appreciated that the acts and symbolically represented operations or instructions include the manipulation of electrical signals by the processing unit. An electrical system with data bits causes a resulting transformation or reduction of the electrical signal representation, and the maintenance of data bits at memory locations in the memory system to thereby reconfigure or otherwise alter the processing unit's operation, as well as other processing of signals. The memory locations where data bits are maintained are physical locations that have particular electrical, magnetic, optical, or organic properties corresponding to the data bits.

The data bits may also be maintained on a computer readable medium including magnetic disks, optical disks, organic disks, and any other volatile or non-volatile mass storage system readable by the processing unit. The computer readable medium includes cooperating or interconnected computer readable media, which exist exclusively on the processing system or is distributed among multiple interconnected processing systems that may be local or remote to the processing system.

In preferred embodiments, the ultrasound imaging system includes color and power Doppler modes to detect the presence, direction and relative velocity of blood flow by assigning color-coded information to these parameters. The color is depicted in a region of interest that is overlaid on to the B-mode image. All forms of ultrasound-based imaging of red blood cells are derived from the echo signal that is received in response to the transmitted signal. The primary characteristics of this signal are its frequency and its amplitude (or power). The frequency shift is determined by the movement of the red blood cells. The amplitude is dependent on the amount of blood in motion present within the volume that is sampled by the ultrasound beam.

Figure 5:
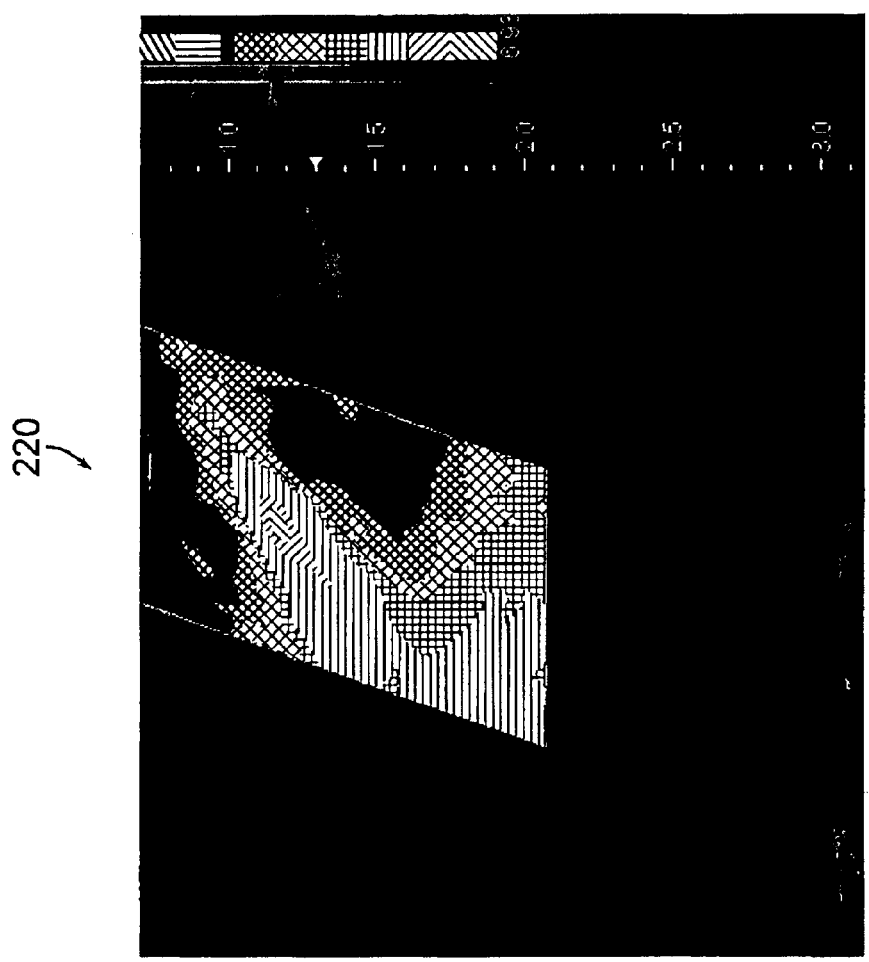
FIG. 5 is a view of a display screen showing an ultrasound image illustrating the color Doppler mode in accordance with a preferred embodiment of the present invention.

In a preferred embodiment, as illustrated in FIG. 5, color Doppler allows flow velocity information to be detected over a portion of the B-Mode image. The mean Doppler shift is then displayed against a gray scale representation of the structures. Color Doppler images display blood flow by mapping the frequency shift (velocity) of blood cells. Flow towards the transducer is assigned shades of red, and flow away from the transducer is displayed in shades of blue. Alternate embodiments can use different color contrasts. Higher frequencies are displayed in lighter colors and lower frequencies in darker colors. For example, the proximal carotid artery is normally displayed in hues of bright red and orange because the flow is toward the transducer and the frequency (velocity) of flow in this artery is relatively high. By comparison, the flow in the jugular vein is displayed as blue because it flows away from the transducer.

Figure 6B:
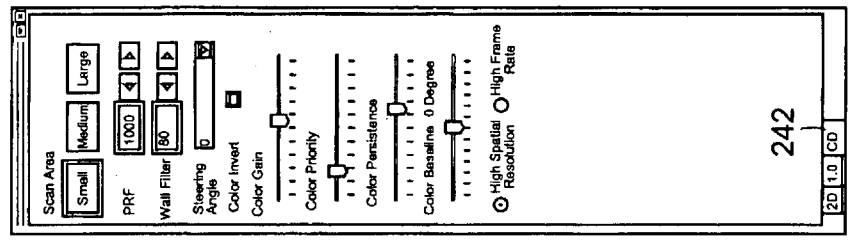
FIGS. 6A and 6B illustrate a view of a display screen showing the color Doppler mode of an ultrasound image and the available controls, respectively, in accordance with a preferred embodiment of the present invention.
Figure 6A:
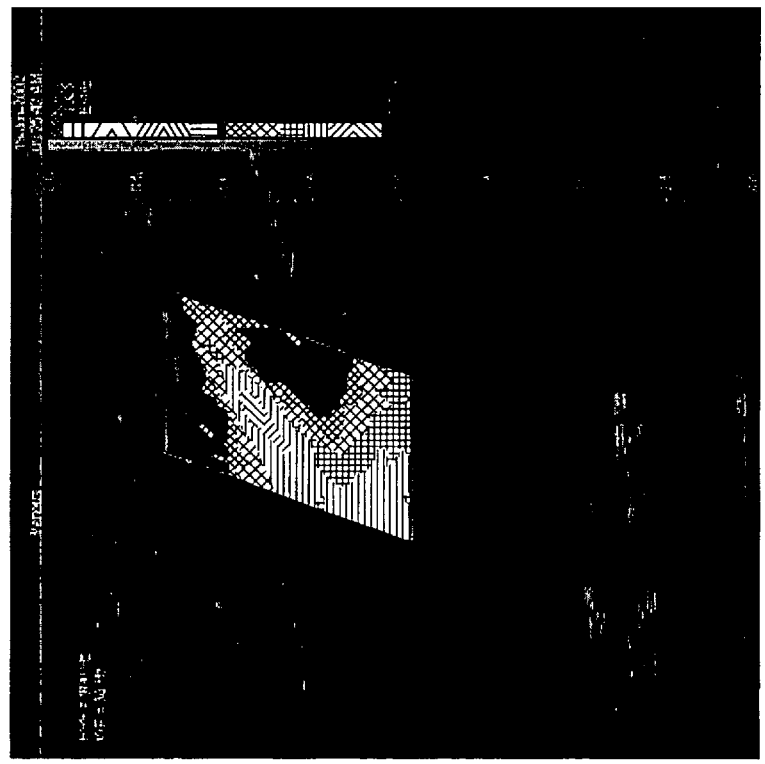
Figure 7A:
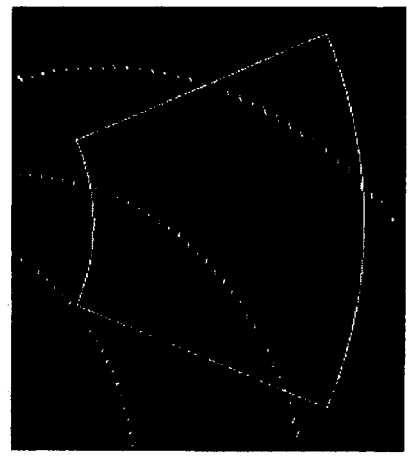
FIGS. 7A–7D illustrate the controls and image sizes available by adjusting the scan area, respectively, in accordance with a preferred embodiment of the present invention.
Figure 7C:
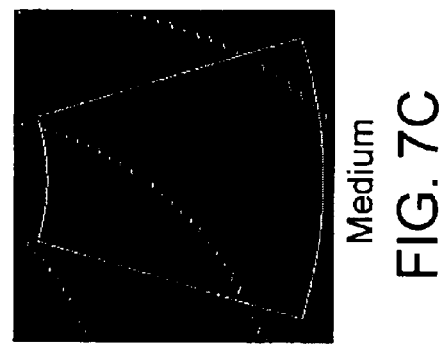
Figure 7B:
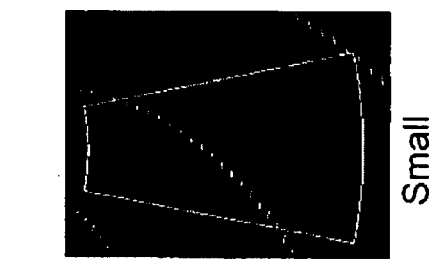
Figure 7D:

The color Doppler mode provides, in preferred embodiments, fourteen examination types to provide presets depending upon the probes used. The range of WF includes 1% to 25% of pulse repetition frequency (PRF), and steering angles include, for example, +/−15°, +/−20°, and 0 for flat linear probes. Further, maps in red/blue based on velocity of blood flow and high spatial resolution versus high frame rate for certain probes is also provided. In a preferred embodiment, as illustrated in FIG. 6A and 6B the color Doppler (CD)-mode for image display is selected by choosing the CD-mode button from a image mode bar, or from a Modes menu. To select the CD image control setting, the user selects the CD tab 242 at the bottom of the image control bar. The scan area controls the size of the region of interest. Further, in preferred embodiments the Doppler systems use a wall filter to reduce and preferably eliminate unwanted low frequency signals from the display. The color controls 244*a–d* can be adjusted to increase the quality of an image.

FIGS. 7A–7D illustrate the controls and the image sizes available in a color Doppler mode in accordance with a preferred embodiment. The size of the scan area is one of the controls the user manipulates to affect the frame rate. The smaller the scan area, the faster the frame rate. Alternatively, the larger the scan area, the slower the frame rate. For example, for cardiac or arterial applications, a small scan area can be used to accurately visualize the flow dynamics. A medium or large scan can also be used for applications where the blood flow dynamics do not change rapidly over time, or if the user wants to get a larger overall view of the blood flow.

Figure 8A:
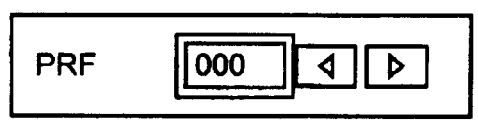
FIGS. 8A–8D illustrate the controls available for adjusting different parameters such as pulse repetition frequency, wall filter, steering angle and color inversion for a color Doppler mode in accordance with a preferred embodiment of the present invention.

In a preferred embodiment, as shown in FIG. 8A, the ultrasound system provides for adjustment of the pulse repetition frequency (PRF). The PRF adjusts the range of the velocity display shown on a color bar. Decreasing the PRF values improves the display of slow blood flow. The maximum value for the PRF is dependent on the specific probe that is being used and how deep the region of interest is. The PRF can be set high enough to prevent aliasing, and low enough to provide adequate detection of low flow. It may be necessary to vary the PRF during an examination, depending on the speed of the blood flow, and/or if a pathology is present. If the PRF is set too high, low frequency shifts caused by low velocity flow may not be shown. In preferred embodiments, the PRF is set higher for cardiac and arterial applications than it is for venous or small parts application.

Figure 8B:
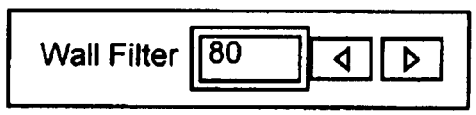

In a preferred embodiment, Doppler systems use a wall filter to eliminate unwanted low frequency signals from the display. Raising the wall filter reduces the display of low velocity tissue motion. As illustrated in FIG. 8B, the ultrasound system provides for an adjustment of a wall filter. As the wall filter is lowered, more information is displayed, however, more wall tissue motion can also be displayed. The wall filter can range from 1% to 25% of the PRF (in increments of 2, 10, 25, 50 or 100 depending on the wall filter value). The wall filter is set high enough so that color Doppler flash artifacts from tissue or wall motion are not displayed, but low enough to display slow flow. If the wall filter is set too high, slower flow may not be seen. The wall filter is set higher for applications where there is significant tissue motion (such as a cardiac application), or in instances where the probe is moved rapidly while color Doppler is on. It may be set lower for small parts or instances where flow is slow but there is not much tissue motion.

Figure 8C:
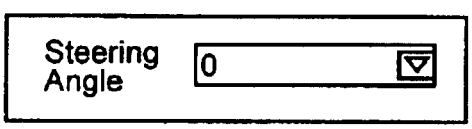

A preferred embodiment also provides for the adjustment of a steering angle as shown in FIG. 8C. The steering angle is used only on flat linear arrays, and allows adjustments for optimal angle between beam and flow. The angle range is, but not limited to, for example, 0, +/−15°, +/−20°. Doppler angle adjustment is important in obtaining adequate signals and in interpreting the color Doppler examination. Changes in the angle of the Doppler beam to the path of flow causes changes in the color Doppler display. When using color Doppler, the user has to be aware of the Doppler angle to flow. At a 90 degree angle to flow, an absent or confusing color pattern is displayed (even when the flow is normal). An adequate Doppler angle to flow is required in order to obtain useful color Doppler information. In most instances, the lower the angle of the color Doppler beam to flow, the better the received signal. Electronic steering is useful in the embodiments where the flow is at a poor angle to the color Doppler beam. However, in many embodiments it is also necessary to use the "heel to toe" technique, which involves using pressure on one end of the probe or the other to improve the Doppler angle to flow. It should be noted that curved linear and phased array probes do not have the capability of electronic steering and depending on the clinical situation, may require the use of the "heel and toe" technique to obtain an adequate angle to flow. As color Doppler is angle dependent, a weak flow signal results if the vessel is approximately at 90 degrees to the beam.

Figure 8D:
Figures 9A, 9B:
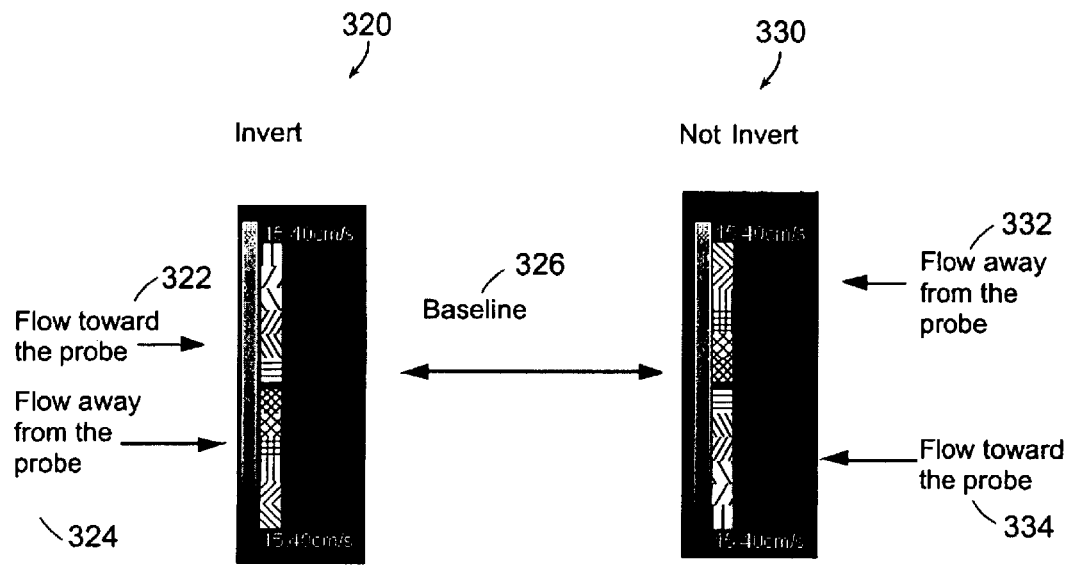
FIGS. 9A and 9B illustrate the color Doppler reference bar that is used for a color invert adjustment in accordance with a preferred embodiment of the present invention.

Another preferred embodiment includes the provision of color inversion. When the user chooses the Color Invert box illustrated in FIG. 8D, the color Doppler reference bar is inverted as well as the color within the region of interest. The color reference bar is divided by a zero baseline. To invert the color Doppler reference bar, the user can click on the Color Invert box. The Play button is used to see the Color Invert effect on a frozen image. Conventionally, the color red is assigned to positive frequency shifts (flow toward the probe), and blue is assigned to negative frequency shifts (or flow away from the probe). However, this color assignment can be reversed at the user's discretion by selecting Invert. Whether or not the user has inverted the display, flow toward the probe is assigned the colors of the top half of the color bar, and flow away from the probe is assigned the colors of the bottom half of the color bar. FIGS. 9A and 9B illustrate the inverted and non-inverted reference bar in the color Doppler mode. Invert may be used when scanning the internal carotid artery (ICA), for example. In general, flow in this vessel goes away from the probe. If Invert is enabled, the ICA flow is displayed in shades of red. The color bar then displays shades of blue on the top half, and a shade of red on the bottom.

Figure 10:
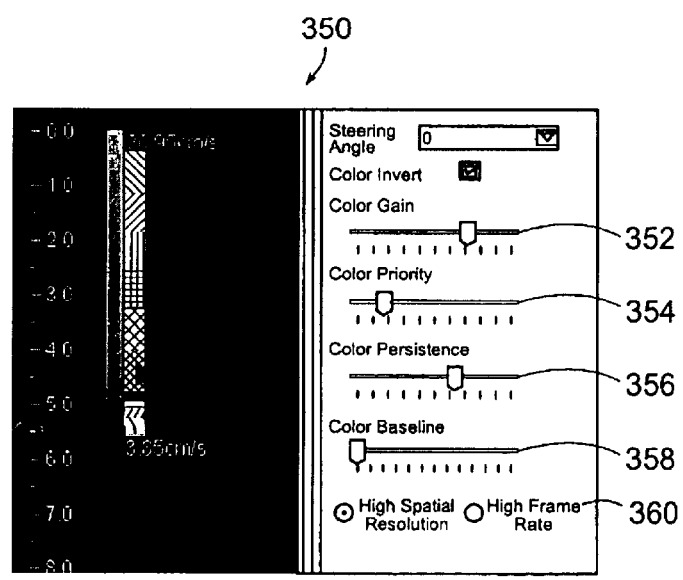
FIG. 10 illustrates additional adjustments available to a user in the color Doppler mode such as color gain, color priority, color persistence and color baseline in accordance with a preferred embodiment of the present invention.

Preferred embodiments also allow for the adjustment of the color gain which increases or decreases the amplification of the returning signal displayed or being played. The color gain adjustment 352 is illustrated in FIG. 10. The color gain can be increased whenever the fill of color within a vessel is inadequate, and can be decreased whenever an unacceptable amount of color is seen outside of a vessel.

Preferred embodiments also accommodate the adjusting of the color priority of the image which defines the amount of color displayed over bright echoes and helps confine color within the vessel walls. This adjustment in color priority 354 is illustrated in FIG. 10. This control affects the level at which color information overwrites the B-mode information. If the user needs to see more flow in an area of some significant B-mode brightness, they increase the color priority. If a user wants to better contain the display of flow within the vessel(s), they decrease the color priority. If, however, the color priority is set all the way to the left, no color is displayed.

A preferred embodiment also accommodates for adjusting the color persistence as illustrated in FIG. 10. The color persistence adjustment 356 averages frames of color. Increasing the persistence causes the display of flow to persist on the 2D image. Decreasing the persistence allows better detection of short duration jets, and provides a basis for better flow/no flow decisions. Adjusting color persistence also produces better vessel contour depiction. To adjust the color persistence for a scan, in a preferred embodiment, the slider is moved to the right or left to achieve the desired image. When color persistence is set high, the saved image (single frame) may not look exactly the same as when the image is saved. The user receives a warning when this occurs; however, this does not occur when exporting images.

In a preferred embodiment, as illustrated in FIG. 10, the color baseline 358 can also be adjusted. The baseline refers to the zero baseline within the color Doppler window. Adjusting this control moves the zero baseline up or down. To adjust the baseline, the slider is moved to the right or left to achieve the desired range of degree. In general, it is not necessary to adjust the color baseline. If the user does adjust it, moving the baseline down displays more positive flow and moving the baseline up displays more negative flow in an embodiment. When the user adjusts the color baseline, they are able to display more forward or reversed flow. This adjustment can be used to prevent aliasing in either direction.

Further embodiments include an adjustment for high frame rate 360 shown in FIG. 10. This control adjusts the line density within the Doppler region of interest. The user can choose between an image with higher line density resulting in better spatial resolution or lower line density resulting in a better frame rate. The high frame rate is used when the flow rate is high such as in cardiac or certain arterial applications. This control is available with certain embodiments of the probes. When the user selects high spatial resolution, line density is increased. However, when the user selects high frame rate, line density is decreased.

Another preferred embodiment of the present invention includes a directional power Doppler mode which can be viewed as a combination of both conventional power Doppler and color Doppler modes. It provides the same increased sensitivity as conventional power Doppler as well as directional information derived from color Doppler. Directional power Doppler does not provide an estimate of the frequency (velocity) of blood flow. The color palette is proportional to the strength of the Doppler signal. The mode allows the user to achieve good image quality of deep arteries and other tissue. One also has the option to apply a high frame rate or high resolution to control the quality of the scan. The benefits of directional power Doppler include examination types to provide presets (dependent upon certain probes), Doppler steering angles of (+/−15°,=/−20°, 0°, for linear probes), without limitation, range of WF and increments (2 to PRF/4 Hz) and increased Doppler sensitivity performance.

Figure 11B:
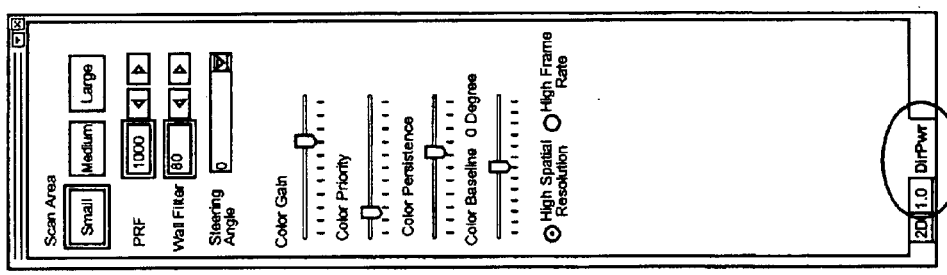
FIGS. 11A and 11B illustrate the images and controls provided by direction power Doppler, respectively, in accordance with a preferred embodiment of the present invention.
Figure 11A:
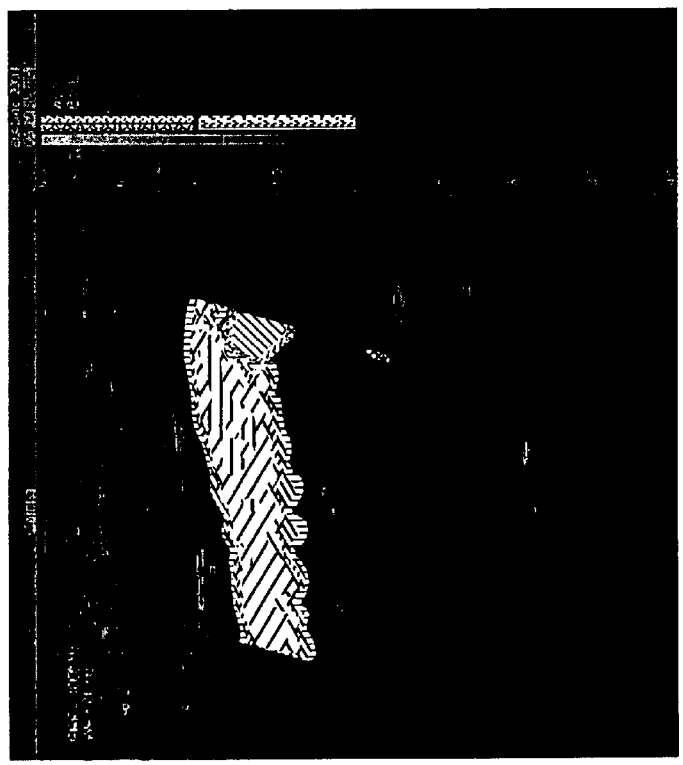

As illustrated in FIGS. 11A and 11B, the DirPwr-mode 382 is selected and for image display, the DirPwr-mode button from the image mode bar can be chosen, or from the Modes menu. To select the DirPwr image control setting, the user selects the DirPwr tab at the bottom of the image control bar. Similar to the color Doppler mode, the scan area controls-the size of the region of interest. The Doppler systems use the wall filter to eliminate unwanted low frequency and provides color control adjustments.

As illustrated hereinbefore, the scan can be adjusted even in the directional power Doppler mode. The size of the scan area is one of the controls that is used to affect the frame rate. The smaller the scan area, the faster the frame rate. Alternatively, the larger the scan areas, the slower the frame rate. For cardiac or arterial applications, a small scan area is used to accurately visualize the flow dynamics. A medium or large scan can also be used for applications where the blood flow dynamics do not change rapidly over time, or if the user wishes to get a larger overall view of the blood flow. The region of interest can be defined by adjusting the scan area. The scan area options range from small, medium to large.

In the directional power Doppler mode, the PRF can be set high enough to prevent aliasing, and low enough to provide adequate detection of low flow. It may be necessary to vary the PRF during one examination depending on the speed of the blood flow, and/or if the pathology is present. If the PRF is set too high, signals caused by slow flow states with few red blood cells may not be shown. In an embodiment, the PRF is set higher for high flow states than it is for low flow states. The PRF can be set high enough to prevent aliasing, and low enough to provide adequate detection of low flow. It may be necessary to vary the PRF during one examination, depending on the speed of the blood flow, and/or if the pathology is present. If flow is weak or slow it is displayed in darker shades. If flow is strong or fast it is shown in brighter shades. Directional power Doppler is somewhat angle dependent. Good Doppler angles can be maintained.

Further, Doppler systems use a wall filter to eliminate unwanted low frequency signals from the display. Raising the wall filter reduces the display of low velocity tissue motion. As the wall filter is lowered, more information is displayed, however, more wall tissue motion is also displayed. The wall filter can be set high enough so that Doppler flash artifacts from tissue or wall motion are not displayed, but can be set low enough to display slow flow. If the wall filter is set too high, slower flow may not be seen. The wall filter is set higher for applications where there is significant tissue motion, or in instances where the probe is moved rapidly while directional power Doppler is enabled. It may be set lower for small parts or instances where flow is weak but there is not much tissue motion. The wall filter range is dependent on which probes the user is using as well as the PRF setting. Wall filter range is from 1% to 25% of the PRF (in increments of 2, 10, 25, 50 or 100 depending on the wall filter value).

In addition, the steering angle adjusts the optimal angle to flow in the direction power Doppler mode. The steering angle is used only on linear arrays, and allows adjustments for optimal angle between beam and flow. The angle range is without limitation, 0, +/−15°, +/−20°. The steering angle adjusts the optimal angle to flow. Doppler angle adjustment is important in obtaining adequate signals and in interpreting the color Doppler examination. Changes in the angle of the Doppler beam to the path of flow causes changes in the color Doppler display. When using color Doppler the user has to be aware of the Doppler angle to flow. At a 90 degree angle to flow, an absent or confusing color pattern is displayed (even when the flow is normal). An adequate Doppler angle to flow is required in order to obtain useful color Doppler information. In most instances, the lower the angle of the color Doppler beam to flow, the better the received signal. Electronic steering is available for flat linear array probes. Electronic steering is useful in preferred embodiments in those instances where the flow is at a poor angle to the color Doppler beam. However, in many instances it is also necessary to use the "heel and tow" technique, which involves using pressure on one end of the probe or the other to improve the Doppler angle to flow. Curved linear and phased array probes do not have the capability of electronic steering and depending on the clinical situation, may require you to use the "heel and toe" technique to obtain an adequate angle to flow. To change the steering angle, the down arrow is clicked and the desired setting is selected.

In an embodiment including directional power Doppler, the user can adjust the color gain which increases or decreases the amplification of the returning signal displayed or being played. Color gain can be increased whenever the fill or color within a vessel is inadequate, and should be decreased whenever an unacceptable amount of color is seen outside of a vessel.

Further, in an embodiment including directional power Doppler, color priority can be adjusted. This control affects the level at which color information overwrites the B-mode information. If the user needs to see more flow in an area of some significant B-mode brightness, the color priority is increased. If the user wants to better contain the display of flow within the vessel(s), they decrease the color priority. To adjust the color priority the slider is moved to the right or left to achieve the desired range. Raising the priority displays color on brighter structures. Lowering priority increases containment of the display of flow to within the vessels. If, however, color priority is set all the way to the left, no color will be displayed.

The color persistence can be adjusted which averages frames of color. Increasing the persistence causes the display of flow to persist on the 2D image. Decreasing the persistence allows better detection of short duration jets, and provides a basis for better flow/no flow decisions. Adjusting color persistence also produces better vessel contour depiction.

Further, in the preferred embodiment it is not necessary to adjust the color baseline. If the user does not wish to adjust it, moving the baseline down displays more positive flow and moving the baseline up displays more negative flow. When you adjust the color baseline, you are able to display more forward or reversed flow. This adjustment can be used to prevent aliasing in either one direction.

The preferred embodiment includes a high frame rate adjustment. This control adjusts the line density within the Doppler region of interest. The user can choose between one image with higher line density resulting in better spatial resolution or lower line density resulting in better frame rate. High frame rate is used when the flow rate is high such as in cardiac or certain arterial applications. This control is only available on certain probes.

Conventional power Doppler in accordance with a preferred embodiment images blood flow by displaying the density of red blood cells, as opposed to their velocity. Large amplitude signals are assigned a bright hue and weak signals are assigned a dim hue. All flow is displayed in shades of the same color. No directional information is provided in this embodiment.

In accordance with another embodiment, the ultrasound imaging system includes a power Doppler mode. The sensitivity of power Doppler is greater than color Doppler. Amplitude estimation in this mode is less noisy than a mean frequency estimate, therefore more real signal is detected and displayed with the power Doppler mode. Power Doppler is also less angle dependent than Color Doppler because of this increase in sensitivity, and does not alias. All flow is displayed in shades of the same color, however, no directional information is provided. The benefits of power Doppler include it being more sensitive to low flow than color or direction power Doppler, it is the preferred mode to show perfusion and contour of vessel lumen and large amplitude signals are assigned a bright hue and weak signals are assigned a dim hue. For example, the jugular vein is shown in brighter colors than the carotid artery because the vein contains more red blood cells at any given time than does the artery.

Figures 12A, 12B:
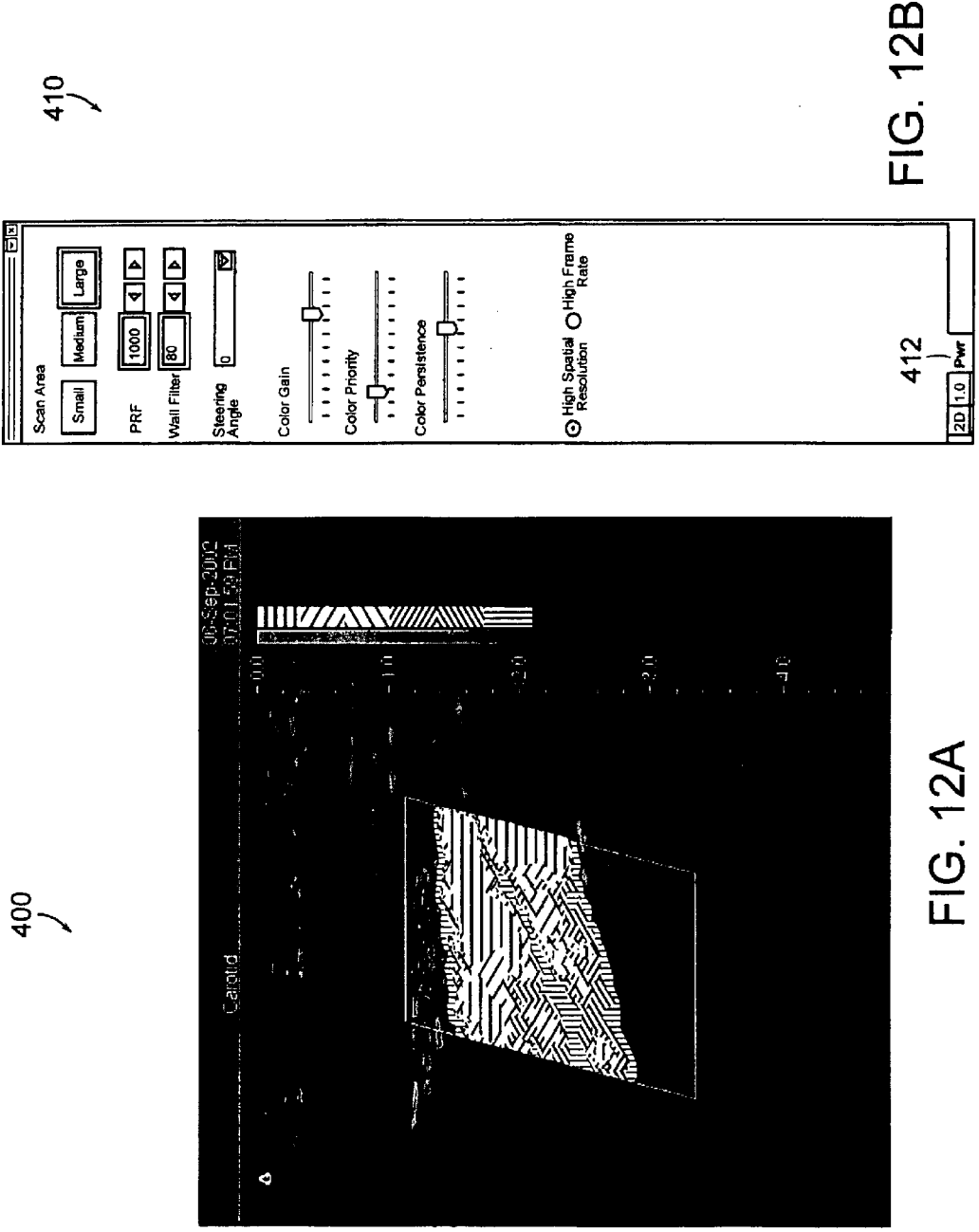
FIGS. 12A and 12B illustrate an image and the controls provided to a user in a power Doppler mode in accordance with a preferred embodiment of the present invention.

To select the Pwr-mode for image display, the user select a Pwr-mode button from the image mode bar, or from the Modes menu as illustrated in FIGS. 12A and 12B. To select the Pwr image control setting, the user selects the Pwr tab 412 at the bottom of the image control bar. Increasing the PRF increases the range of the display. Lower PRF values improve the display of slow flow. PRF is dependent on the specific probe that is being used.

In the embodiment including power Doppler mode, the size of the scan area is one of the controls the user has access to that most affects the frame. The smaller the scan area, the faster the frame rate. Alternatively, the larger the scan area, the slower the frame rate. For cardiac or arterial applications, a small scan area is used to accurately visualize the flow dynamics. A medium or large scan can also be used for applications where the blood flow dynamics do not change rapidly over time, or if the user wishes to get a larger overall view of the blood flow. The region of interest can be defined by adjusting the scan area. The scan area options range from small, medium to large as previously described.

In the power Doppler mode, the PRF (Pulse Repetition Frequency) can be low enough to provide adequate detection of low amplitude flow. It may be necessary to vary the PRF during one examination depending on the speed of the blood flow, and/or if the pathology is present. If the PRF is set too high, signals caused by slow flow states with few red blood cells may not be shown. The PRF is set higher for high flow states than it is for flow states in most preferred embodiments. To increase the PRF, the right arrow is selected. To decrease the PRF, the left arrow in a control is selected. The PRF values range from 100 Hz to 15 kHz and depend upon the probe being used. If there are few red blood cells being sampled, flow is shown in the darker shades of gold. If there are many red blood cells being sampled, flow is displayed in a brighter shade of gold. Power Doppler is the least angle dependent Doppler mode. However, it is good practice to maintain reasonable Doppler angles while using this mode.

In an embodiment including power Doppler mode, a wall filter can be set high enough so that power Doppler flash artifacts from tissue or wall motion are not displayed. However, the wall filter can be set low enough to display low amplitude signals. If the wall filter is set too high, low amplitude signals may not be seen. The wall filter is set higher for applications where there is significant tissue motion, or in instances where the probe is moved rapidly while power Doppler is on. It may be set lower for small parts or instances where the amount of blood flow is small and there is not much tissue motion.

With respect to adjusting the steering angle, power Doppler is less angle dependent than Color Doppler, but many of the same rules still apply. Changes in the angle of the Doppler beam to the path of flow causes changes in the power Doppler display. At 90 degrees to flow, a weak signal may be displayed even when the flow is normal. The steering angle adjusts the optimal angle to flow. To increase the steering angle, the down arrow to the desired setting is selected. The angle range is, for example, –0, +/–15, +/–20 without limitation. If an adequate angle is used, the Doppler angle and the quality of the received signal is enhanced. The more red cells being sampled the stronger the received signal. Further, attenuation plays a role in the strength of the displayed signal. The closer the area of interest is to the probe, the less the attenuation and the stronger the received signal. In a preferred embodiment, electronic steering is available for flat linear array probes. Electronic steering is useful in those instances where the flow is at a poor angle to the power Doppler beam. In many instances, it is also necessary to use the "heel and toe" technique, which involves using pressure on one end of the probe or the other to improve the Doppler angle to flow. Curved linear and phased array probes do not have the capability of electronic steering and depending upon the clinical situation, may require you to use the "heel and toe" technique to obtain an adequate angle to flow.

Embodiments including power Doppler also provide for adjusting color gain. Color gain can be increased whenever the fill of color within a vessel is inadequate, and should be decreased whenever an unacceptable amount of color is seen outside of a vessel. The user can adjust the color gain which modifies the degree of sensitivity to receive signals and increases or decreases the amplification of the returning signal displayed/played. To adjust the color gain, the slider is moved to the right or left to achieve the desired gain. The color gain maximum amplitude is, for example, 1 to 30 units.

In a preferred embodiment including a power Doppler mode, the color priority control affects the level at which color information overwrites the B-mode information. If the user needs to see more flow in an area of some significant B-mode brightness, the color priority is increased. If the user wants to better contain the display of flow within the vessel(s), they decrease the color priority. To adjust the color priority the slider is moved to the right or left to achieve the desired range. Raising the priority displays color on brighter structures. Lowering priority increases containment of the display of flow to within the vessels. The color priority maximum amplitude is, for example, in the range of 1 to 30 units.

Preferred embodiments of the power Doppler mode include adjusting the color persistence which averages frames of color. Increasing the persistence causes the display of flow to persist on the two-dimensional image. Decreasing the persistence allows better detection of short duration jets, and provides a basis for better flow/no flow decisions. Adjusting color persistence also produces better vessel contour depiction.

In an embodiment, the user has the option of selecting a high frame rate versus a high quality image. If the user wants a high quality image, the button for high spatial resolution is selected. If the user wants a high frame rate, the button for high frame rate is selected. When the user selects high spatial resolution, line density is increased. When the user selects high frame rate, line density is decreased.

A preferred embodiment includes a pulsed wave Doppler mode, which is a mode of scanning in which a series of pulses are used to study the motion of blood flow at a small region along a desired scanline, called the sample volume or sample gate. As illustrated in FIG. 13A and 13B the x axis of the graph represents time while the y axis represents Doppler frequency shift. The real-time mixed mode is provided that shows the B-mode scan area (FIG. 13A) along with a bottom window (FIG. 13B) that displays the pulsed Doppler waveform. The shift in frequency between successive ultrasound pulses caused mainly by moving red blood cells, can be converted into velocity if an appropriate angle between the insonating beam and blood flow is known. The strength of the signal appears as shades of gray, for example, in this spectral display. The thickness of the spectral signal is indicative of laminar or turbulent flow (laminar flow typically shows a narrow band of blood flow information). In a preferred embodiment, pulsed wave Doppler and B-mode are shown together in a mixed mode display. This provides the user with the capability of monitoring the exact location of the sample volume on the B-mode image while doing pulsed wave Doppler. The benefits of pulsed wave Doppler include a plurality of examination types, for example, fourteen examination types to provide presets, the range of wall filter is between 1% to 25% of the Pulsed Repetition Frequency (PRF), measurements are available for all examination types including peak systole (PS), end diastole (ED), Resistive Index (RI), and systole-diastole ratio (PS/ED) and duplex imaging is available for real-time display using B-mode and pulsed wave Doppler. The pulse wave Doppler (PWD) mode is selected for image display by selecting a PWD mode button from the image mode bar, or from the modes menu. The PWD image control setting is selected using the PWD tab 452 at the bottom of the image control bar.

In a preferred embodiment of a pulsed wave Doppler mode, there are three sweep speeds available. Further, adjustments to the velocity display are available which changes the unit of the vertical scale within the pulsed wave Doppler window between cm/s and KHz. The centimeter unit is available when the correction angle is situated between 0 and +/−70° in a preferred embodiment.

Preferred embodiments of the pulsed wave Doppler window include adjustments to the PRF (Pulse Repetition Frequency) which adjusts the velocity range of the display. The maximum value for PRF is dependent on the specific probe that is being used and the location of the sample volume. As PRF increases, the maximum Doppler shift that can be displayed without aliasing also increases. Lower PRF values improves the display of slow blood flow. Increasing the PRF also increases the thermal index value.

In a preferred embodiment including the pulsed wave Doppler mode, a wall filter (high pass frequency filter) is used to reduce and preferably eliminate unwanted low frequency high-intensity signals (also known as clutter) from the display. Clutter can be caused by tissue motion or by rapid movement of the probe. A wall filter that is high enough to remove clutter is used but that is low enough to display spectral information near the baseline. The range of wall filter values is, for example, between 1% and 25% of the PRF value.

Preferred embodiment of the pulsed wave Doppler mode include adjusting the steering angle. The steering angle is used only on flat linear arrays, and allows adjustment for optimal angle between beam and flow. The Doppler signal is weak when the angle between the insonating beam and blood flow approximates 90 degrees. Angles of 60° or less are recommended for steering angle. The steering angle does not directly affect the calibration of the velocity scale.

A preferred embodiment also provides for adjusting an invert option. The user can invert the pulsed Doppler waveform. The Doppler scale is separated by a zero baseline that extends across the width of the spectral display. The data above the baseline is classified as forward flow. The data below the baseline is classified as reverse flow. When inverted, the reverse flow displays above the baseline and the forward flow appears below the baseline. To invert the flow, an Invert box is selected.

A preferred embodiment also includes the provision of adjusting a correcting angle in the pulsed wave Doppler mode. To obtain accurate velocities, the user maintains Doppler angles of 600 or less. However, the user can employ higher values of correction angle, especially in peripheral vascular applications where the blood vessels are more parallel to the face of the probe. In a preferred embodiment the maximum value for the correction angle is +/−70°. Velocity display in cm/s is shown only in the range between 0 and +/−70°. Above 70°, the error in the velocity calculation is too large and the velocity scale is converted automatically to frequency, independent of the correction angle. However, the flow direction cursor is shown on the screen for reference. The correction angle control is active also on frozen images. To adjust the correction angle, the user selects the left and right arrows in the Correction Angle field and clicks to the desired value setting. Or, in the alternative, the user can employ the quick adjustment key to easily set the angle correction between +/−60° degrees and 0 degrees.

Further, a preferred embodiment provides for adjusting sample volume size and position in the pulsed wave Doppler mode. The user can adjust the size of the pulsed wave Doppler region being examined by setting the sample volume size control. The lower the value, the narrower the sample size used in the calculation of flow velocity contents. To adjust the sample volume size, the user selects the left and right arrows next to the SV Size field to set to the desired value. The value range for sample volume size is, for example, 0.5 to 20 mm (in 0.5 mm increment). The adjustment is visible on the SVgate and Probe Info interface when enabled. The position of the sample volume can be adjusted by using the touch-pad control. Left-click on the sample volume (the line becomes green,) is selected to move it to the desired location, and left-click is selected again to anchor it to make active. Alternatively, this movement can be accomplished by using the keyboard arrow keys. Modifying the depth location of the sample volume affects the thermal index value.

Preferred embodiments of the pulsed wave Doppler mode include the adjustments for gain baseline and sound volume. The user can adjust the gain which increases or decreases the amplification of the returning signal displayed/played. The gain can be adjusted so that the spectral waveform is bright but not so high that the systolic window fills in, or other artifacts are created. The baseline refers to the zero baseline within the Pulsed Wave Doppler window. Adjusting this control moves the zero baseline up or down. When the user adjusts the baseline, they are able to display more forward or reversed flow, taking advantage of the full scale available at that particular PRF value. This adjustment is visible on the reference bar. Adjusting the sound volume control lets the user define the volume of the pulsed wave Doppler. The sound volume of the spectral signal can be adjusted to a comfortable level. If it is too high, system noise may interfere with the sound produced by the blood flow.

It should be understood that the programs, processes, methods and systems described herein are not related or limited to any particular type of computer or network system (hardware or software), unless indicated otherwise. Various types of general purpose or specialized computer systems may be used with or perform operations in accordance with the teachings described herein.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams. While various elements of the preferred embodiments have been described as being implemented in software, in other embodiments hardware or firmware implementations may alternatively be used, and vice-versa.

It will be apparent to those of ordinary skill in the art that methods involved in the system and method for ultrasound imaging may be embodied in a computer program product that includes a computer usable medium. For example, such a computer usable medium can include a readable memory device, such as, a hard drive device, a CD-ROM, a DVD-ROM, or a computer diskette, having computer readable program code segments stored thereon. The computer readable medium can also include a communications or transmission medium, such as, a bus or a communications link, either optical, wired, or wireless having program code segments carried thereon as digital or analog data signals.

The claims should not be read as limited to the described order or elements unless stated to that effect. Therefore, all embodiments that come within the scope and spirit of the following claims and equivalents thereto are claimed as the invention.

What is claimed:

1. A ultrasound system for scanning a region of interest with ultrasound energy to image a fluid moving within the region of interest comprising:
    a transducer array;
    a data processing system connected to the transducer array and including a Doppler processing system having at least one parallel computing element, and a memory coupled to the at least one parallel computing element, the memory having stored therein a sequence of instructions to vectorize radio frequency serial input data for parallel processing, to adjust the pulse repetition frequency and to execute color Doppler processing.

2. The ultrasound system of claim 1, wherein the at least one parallel computing element comprises a multiplier and an adder.

3. The ultrasound system of claim 1, wherein the at least one parallel computing element executes at least one of Single Instruction Multiple Data instructions and Multiple Instruction Multiple Data instructions.

4. The ultrasound system of claim 1, wherein Doppler processing is executed in a computation device having an MMX or floating point processor.

5. The ultrasound system of claim 1, wherein the Doppler processing further comprises directional power Doppler, power Doppler and pulsed wave Doppler and provides corresponding images.

6. The ultrasound system of claim 1, further comprising adjustable controls for one of at least scan area selection, velocity display, steering angles, color inversion, color gain, color priority, color persistence, color baseline and frame rate.

7. In an ultrasound system for Doppler processing, a method for imaging a region of interest comprising of:
    providing a transducer array for capturing data from a region of interest;
    providing a data processing system coupled to the transducer array and having a microprocessor with at least one parallel processing element and a memory coupled to the microprocessor having stored therein a sequence of instructions to vectorize radio frequency serial input data for parallel processing and execute Doppler processing including one of color Doppler, directional power Doppler, power Doppler and pulsed wave Doppler;
    Selectively adjusting the pulse repetition frequency; and
    performing a Doppler processing operation to form an image of the region of interest.

8. A computer readable medium having stored therein instructions for causing a processing unit to execute the steps of the method of claim 7.

9. The method for imaging a region of interest of claim 7, wherein the sequence of instructions to vectorize the serial input data further comprises of:
    mapping a stream of serial RF data to a vector representation;
    determining an auto-correlation function of the data; and
    determining a phase shift of the auto-correlation function to generate a monotonic function for all values of the phase shift corresponding to a range of Doppler velocities.

10. The method of imaging a region of interest of claim 9, wherein the sequence of instructions further comprises:
    demodulating the data to obtain in-phase and quadrature sample data;
    filtering the data to remove low frequency signals;
    averaging a plurality of frames of data;
    converting phase shift data to an index;
    converting the phase shift data from scan to raster coordinates; and
    displaying a plurality of images.

11. The method for imaging a region of interest of claim 7, wherein at least one parallel processing element comprises a multiplier and an adder.

12. The method for imaging a region of interest of claim 7, wherein at least one parallel processing element executes at least one of Single Instruction Multiple Data instructions and Multiple Instruction Multiple Data instructions.

13. The method for imaging a region of interest of claim 7, wherein the Doppler processing further comprises displaying at least one of the presence, direction, and relative velocity of blood flow, perfusion and contour of lumens.

14. The method of imaging a region of interest of claim 7, further comprising providing adjustable controls for at least one of scan area selection, velocity display, steering angles, color inversion, color gain, color priority, color persistence, color baseline and frame rate.

15. The method of claim 7 further comprising processing floating point values.

16. An ultrasound imaging apparatus comprising:
    at least one processing module; and
    memory operable coupled to the at least one processing module, wherein the memory stores operational instructions that cause the at least one processing module to:
    map serial data to vector representation;

calculate an auto-correlation function of the data;

calculate a phase shift of the auto-correlation function to generate a monotonic function for all values of the phase shift corresponding to a range of Doppler velocities;

convert the phase shift to an index; and display a plurality of images including at least one of color Doppler, directional power Doppler, power Doppler and pulsed wave Doppler.

17. The apparatus of claim 16, wherein the apparatus further comprises a handheld probe operable to transmit an ultrasound image and to obtain data indicative of the flow characteristics of the region of interest.

18. The apparatus of claim 16, wherein the plurality of images includes color Doppler images, directional power Doppler images, power Doppler images and pulsed wave Doppler images.

19. The apparatus of claim 16, further comprising adjustable controls for one of at least scan area selection, velocity display, steering angles, color inversion, color gain, color priority, color persistence, color baseline and frame rate.

20. The apparatus of claim 16 further comprising demodulating the data to obtain in phase and quadrature sample data.

* * * * *

UNITED STATES PATENT AND TRADEMARK OFFICE
CERTIFICATE OF CORRECTION

PATENT NO. : 7,223,242 B2
APPLICATION NO. : 10/259251
DATED : May 29, 2007
INVENTOR(S) : Xingbai He et al.

It is certified that error appears in the above-identified patent and that said Letters Patent is hereby corrected as shown below:

Column 1, line 5, "of U.S." should read --of co-pending U.S.--;

Column 1, line 6, "2001." should read --2001 and now U.S. Patent No. 6,638,226.--;

Column 1, line 35, "with" should read --within--;

Column 2, line 55, "operable" should read --operably--;

Column 4, line 43, "v" should read -- $\bar{v}$ --;

Column 8, line 55 "U.S. patent application Ser. No. 09/449,780," should read --U.S. Patent 6,530,887,--

Column 8, lines 64-65, "U.S. patent application Ser. No. 09/791,491," should read --U.S. Patent 6,783,493,--;

Column 10, lines 14-15, "in co-pending U.S. patent application Ser. No. 09/822,764" should read --in U.S. Patent 6,669,633--;

Column 14, line 29, please insert Equation (33) as follows:
--sign ($\phi(1)$)=sign(sin($\phi(1)$))=sign(Im{R(1)})    (33) --;

Column 19, line 14, "controls-the" should read --controls the--;

Column 25, claim 1, line 37, "A" should read --An--; and

Column 26, claim 7, line 14, "Selectively" should read --selectively--.

Signed and Sealed this
Twenty-seventh Day of September, 2011

David J. Kappos
*Director of the United States Patent and Trademark Office*